US010531822B2

(12) United States Patent
Montagu et al.

(10) Patent No.: US 10,531,822 B2
(45) Date of Patent: Jan. 14, 2020

(54) FILTERING IN PRE-EVACUATED CONTAINERS

(71) Applicant: Jean I. Montagu, Cambridge, MA (US)

(72) Inventors: Jean I Montagu, Cambridge, MA (US); William Bell, Brookline, MA (US); Sasha Montagu, Whitefish, MT (US)

(73) Assignee: Jean I. Montagu, Cambridge, MA (US)

( * ) Notice: Subject to any disclaimer, the term of this patent is extended or adjusted under 35 U.S.C. 154(b) by 0 days.

(21) Appl. No.: 15/330,225

(22) Filed: Aug. 27, 2016

(65) Prior Publication Data

US 2017/0065217 A1   Mar. 9, 2017

Related U.S. Application Data

(63) Continuation of application No. 13/829,424, filed on Mar. 14, 2013, now Pat. No. 9,427,707.
(Continued)

(51) Int. Cl.
*A61B 5/15* (2006.01)
*A61B 5/154* (2006.01)
(Continued)

(52) U.S. Cl.
CPC ...... *A61B 5/150755* (2013.01); *A61B 5/1411* (2013.01); *A61B 5/15003* (2013.01);
(Continued)

(58) Field of Classification Search
None
See application file for complete search history.

(56) References Cited

U.S. PATENT DOCUMENTS

| 2,460,641 A | 2/1949 | Kleiner |
| 3,814,258 A | 6/1974 | Ayres |

(Continued)

FOREIGN PATENT DOCUMENTS

| JP | 2007/003481 | 1/2007 |
| JP | 2007000536 A * | 1/2007 |

(Continued)

OTHER PUBLICATIONS

Togawa Human Translation—Togawa et al (Year: 2007).*
(Continued)

*Primary Examiner* — Bradley R Spies
(74) *Attorney, Agent, or Firm* — Ivan David Zitkovsky

(57) ABSTRACT

An independent blood filter device depends on flow geometry to deliver blood serum or plasma free of detrimental levels of hemoglobin. It depends critically on an upstream flow rate or pressure differential limiting control element or device that limits the rate of change of pressure differential across the filter element. Pre-evacuated versions can be used to simultaneously draw blood from a living being and provide pressure differential across the filter element between an evacuated collector and a supply end open to atmosphere. A unit pressurized by hand motion employs the external shape of a partially filled blood collection tube as a piston to produce pressure in advance of the control element or device to create the pressure differential across the filter element to a collector vented to atmosphere. The control element or device is disclosed in numerous forms, including specially sized flow constrictions and compliant arrangements.

26 Claims, 17 Drawing Sheets

Related U.S. Application Data

(60) Provisional application No. 61/681,823, filed on Aug. 10, 2012.

(51) Int. Cl.
| | |
|---|---|
| *A61B 5/153* | (2006.01) |
| *A61M 1/02* | (2006.01) |
| *G01N 33/48* | (2006.01) |
| *G01N 33/49* | (2006.01) |
| *B01D 61/22* | (2006.01) |
| *B01D 71/04* | (2006.01) |
| *A61B 5/155* | (2006.01) |

(52) U.S. Cl.
CPC ............. *A61B 5/153* (2013.01); *A61B 5/154* (2013.01); *A61B 5/15074* (2013.01); *A61B 5/150213* (2013.01); *A61B 5/150251* (2013.01); *A61B 5/150351* (2013.01); *A61B 5/150389* (2013.01); *A61B 5/150503* (2013.01); *A61B 5/150946* (2013.01); *A61M 1/0259* (2013.01); *B01D 61/22* (2013.01); *B01D 71/04* (2013.01); *G01N 33/48* (2013.01); *G01N 33/491* (2013.01); *A61B 5/155* (2013.01); *A61B 5/150992* (2013.01)

(56) References Cited

U.S. PATENT DOCUMENTS

| | | | |
|---|---|---|---|
| 4,212,742 A | | 7/1980 | Solomon |
| 4,343,705 A | | 8/1982 | Legg |
| 4,477,575 A | | 10/1984 | Vogel et al. |
| 4,492,634 A | * | 1/1985 | Villa-Real ............. B01D 33/01 210/359 |
| 4,540,492 A | | 9/1985 | Kessler |
| 4,828,716 A | | 5/1989 | McEwen et al. |
| 4,883,068 A | | 11/1989 | Dechow |
| 4,906,375 A | | 3/1990 | Heilmann |
| 4,960,130 A | | 10/1990 | Guirguis |
| 5,030,341 A | | 7/1991 | McEwen et al. |
| 5,181,940 A | | 1/1993 | Bikson et al. |
| 5,308,508 A | | 5/1994 | Womack |
| 5,364,533 A | | 11/1994 | Ogura et al. |
| 5,413,246 A | | 5/1995 | Godolphin et al. |
| 5,423,989 A | * | 6/1995 | Allen ....................... C12Q 1/26 210/488 |
| 5,471,994 A | | 12/1995 | Guirguis |
| 5,555,920 A | | 9/1996 | Godolphin et al. |
| 5,681,529 A | | 10/1997 | Taguchi et al. |
| 5,683,355 A | | 11/1997 | Fini et al. |
| 5,759,866 A | | 6/1998 | Machida et al. |
| 5,876,605 A | | 3/1999 | Kitajima et al. |
| 5,919,356 A | | 7/1999 | Hood |
| 5,979,669 A | | 11/1999 | Kitajima et al. |
| 5,996,811 A | | 12/1999 | Kitajima et al. |
| 6,045,699 A | | 4/2000 | Yazawa et al. |
| 6,170,671 B1 | | 1/2001 | Kitajima et al. |
| 6,225,130 B1 | | 5/2001 | Kitajima et al. |
| 6,261,721 B1 | | 7/2001 | Andrieu et al. |
| 6,264,619 B1 | | 7/2001 | Ferguson |
| 6,406,671 B1 | | 6/2002 | DiCesare et al. |
| 6,410,334 B1 | | 6/2002 | Schmolz |
| 6,465,256 B1 | | 10/2002 | Iskra |
| 6,471,069 B2 | | 10/2002 | Lin et al. |
| 6,479,298 B1 | | 11/2002 | Miller et al. |
| 6,497,325 B1 | | 12/2002 | DiCesare et al. |
| 6,506,167 B1 | | 1/2003 | Ishimito et al. |
| 6,516,953 B1 | | 2/2003 | DiCesare et al. |
| 6,537,503 B1 | | 3/2003 | Conway |
| 6,659,288 B2 | | 12/2003 | Amano et al. |
| 6,659,975 B2 | | 12/2003 | Amano et al. |
| 6,755,802 B2 | | 6/2004 | Bell |
| 6,803,022 B2 | | 10/2004 | DiCesare et al. |
| 6,821,789 B2 | | 11/2004 | Augello et al. |
| 7,070,721 B2 | | 7/2006 | Ji et al. |
| 7,153,477 B2 | | 12/2006 | DiCesare et al. |
| 7,744,820 B2 | | 6/2010 | Togawa et al. |
| 7,767,466 B2 | | 8/2010 | Togawa et al. |
| 7,927,810 B2 | | 4/2011 | Togawa et al. |
| 7,993,847 B2 | | 8/2011 | Togawa et al. |
| 2006/0151510 A1 | | 7/2006 | Matheson |
| 2007/0082370 A1 | | 4/2007 | Togawa et al. |
| 2010/0093551 A1 | | 4/2010 | Montagu |

FOREIGN PATENT DOCUMENTS

| | | |
|---|---|---|
| JP | 2008/232876 | 10/2008 |
| WO | 2007/000966 | 1/2007 |
| WO | 2007/000986 | 1/2007 |

OTHER PUBLICATIONS

International Search Report and Written Opinion dated Nov. 29, 2013 from corresponding PCT application PCT/US2013/050260 issued by EPO now European Patent EP2882340 B1.

* cited by examiner

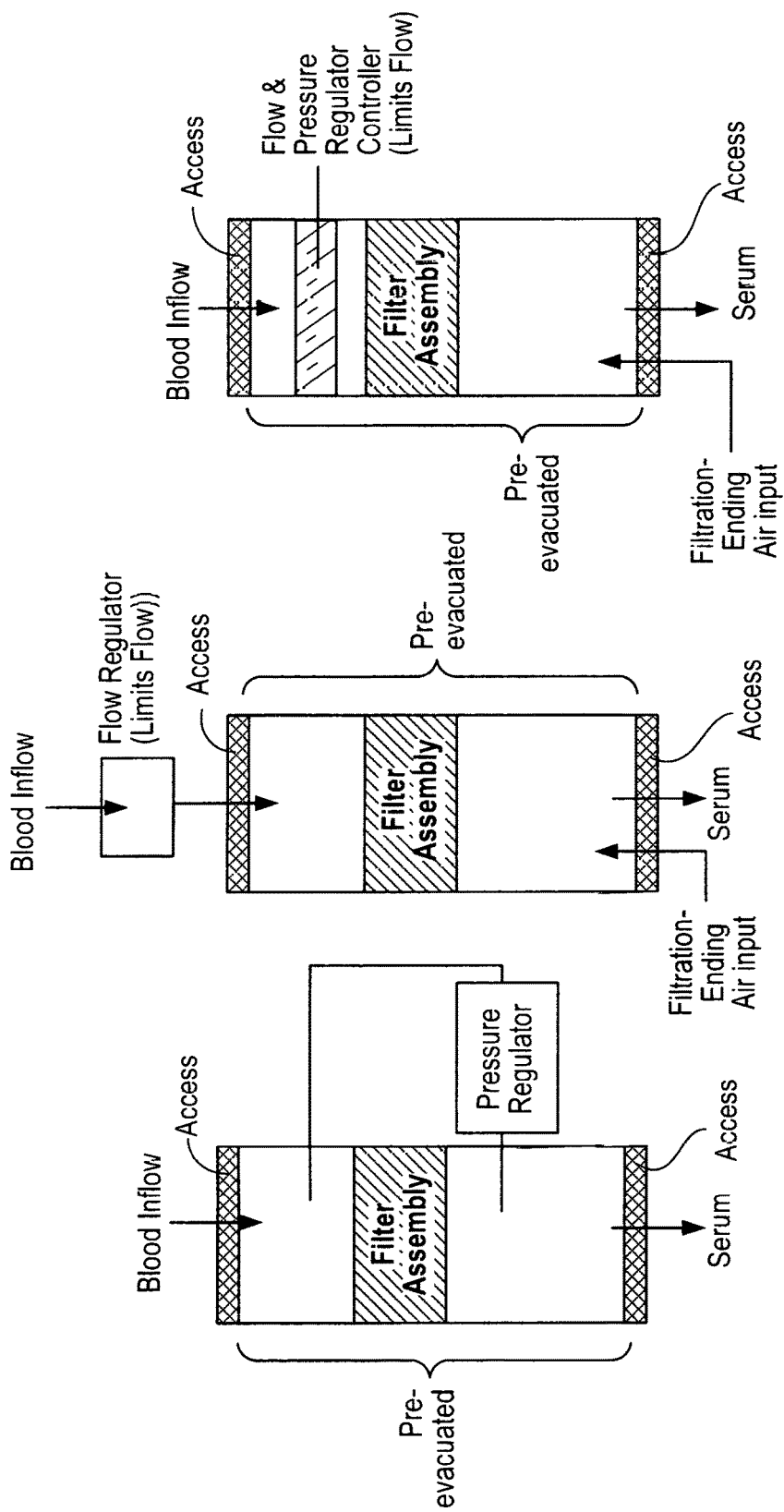

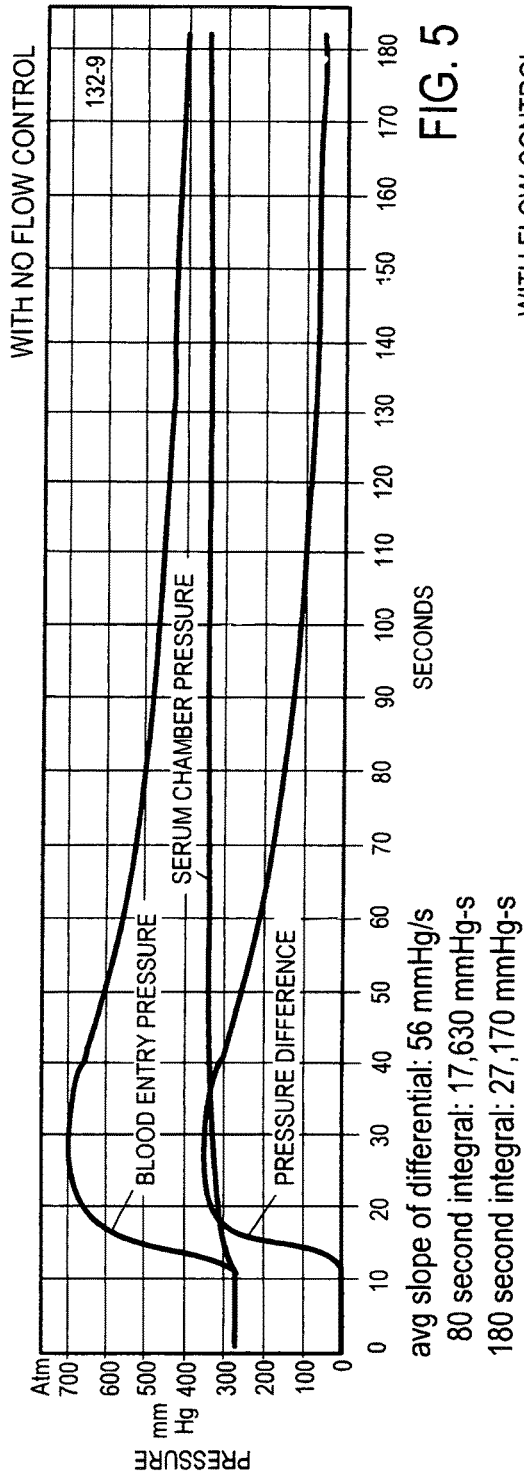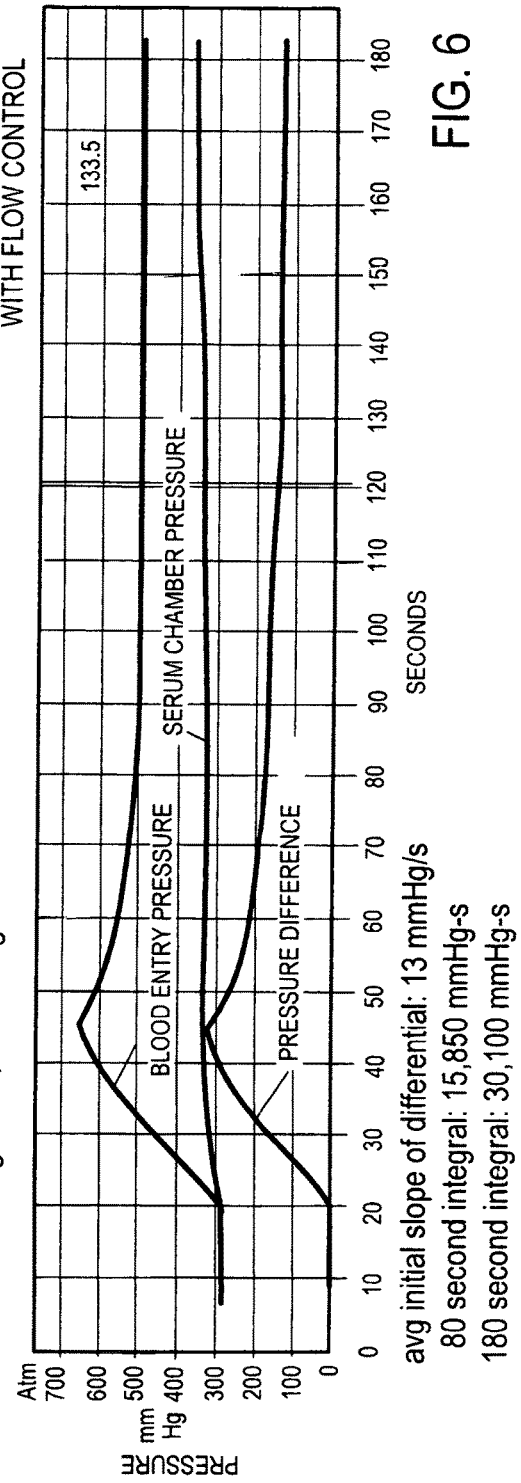

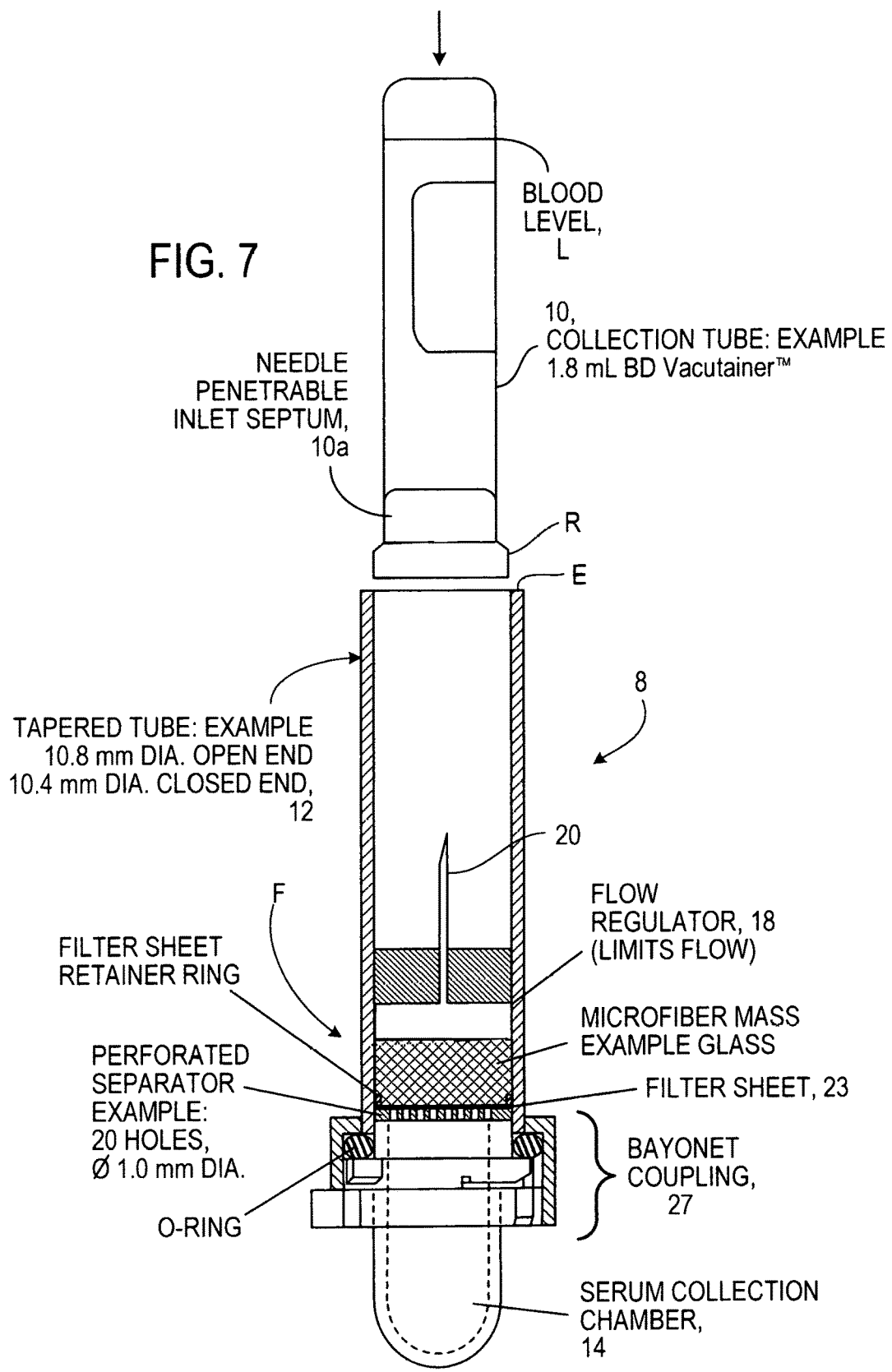

FILTERING IN PRE-EVACUATED CONTAINERS

CROSS-REFERENCE TO RELATED APPLICATION

This application is a continuation of U.S. application Ser. No. 13/829,424, filed Mar. 14, 2013, now U.S. Pat. No. 9,427,707, which claims priority to U.S. Application Ser. No. 61/681,823, filed on Aug. 10, 2012. The above-mentioned applications are hereby incorporated by reference.

TECHNICAL FIELD

This invention relates to extraction of fluid of desired characteristics from a small fluid sample, to isolating relatively large particles from a small sample, and to performing assays and similar activities with the separated substances.

This invention relates specifically to rapid, convenient, inexpensive and sterile extraction of blood plasma, blood serum and other fluid from a small sample of whole blood. It also relates to isolation of blood cells and other components from a small sample, and to using small quantities of a blood-derived, filtered fluid at natural or diluted concentrations to perform bio-array assays and other activities such as diagnostic and analytical procedures. In respect of source of blood to be used, the invention is highly useful in directly drawing blood, and also is highly useful with fresh blood previously drawn within a typical collection tube or otherwise, and with stored blood that has been treated fresh to prevent agglutination.

As used here, "Blood Plasma" refers to the liquid component of whole blood constituting about one half of the volume of the blood, blood cells constituting the remainder of the volume. "Blood Serum" refers to the liquid component of whole blood from which blood cells and blood platelets have been removed.

BACKGROUND

As traditionally conducted, a set of adult blood tests necessitates drawing whole blood with 3 to 6 of the well-known pre-evacuated blood collection tubes (e.g. Vacutainer™, Becton Dickinson and Company, East Rutherford, N.J.), each with typically 2 to 10 milliliter capacity. Plasma or serum is typically obtained when whole blond collected in this fashion is processed by centrifuging or filtering, performed within minutes from the sample being drawn unless a stabilizing substance has been added to permit delayed separation.

The availability of sensitive biological assays has also made it possible to run accurate tests employing much smaller sample volumes than previously employed. For instance, multiple tests are available that can be performed employing less than 0.1 milliliter of the fluid, using bio-array techniques. No very simple, inexpensive and rapidly operable device has been commercially available for providing serum or plasma extraction at this size volume.

Typical delays in obtaining plasma or serum can range from 10 minutes when a centrifuge is on site to over one hour when it is within the facilities. The delay can be days if samples must be transported to remote locations. These delays defeat the value of onsite diagnostics made possible by the new bio-array (biochip) technologies. The major benefit of biochip technology is to offer a diagnosis within 15 to 60 minutes, saving critical time for intervention as well as saving costs.

Small volume whole blood collection, per se, however, has long been available. It was originally developed for blood tests for infants and small animals. For this purpose, evacuated collection tubes have been available for drawing a fraction of a milliliter or a few milliliters of blood. (Extremely small blood volumes have also traditionally been obtained by use of a puncture wound. The finger for instance is pricked with a lancet and then squeezed until a fluid drop of, for example, 10-20 microliters is obtained).

In general, current methods for achieving small volumes of serum from whole blood typically involve numerous steps and employ multiple pieces of equipment and disposable items. Kits are available for these purposes from many sources, examples being: Unopette® (Becton Dickinson and Company); Fisherbrand® microhematocrit and capillary tubes (Fisher Scientific Company, Hampton N.H.); and StatSampler® capillary blood collection kit (StatSpin, Norwood, Mass.). Each of these relies on multiple separate components for performing the functions of sample collection, processing, and recovery.

There have been many attempts to develop more convenient devices, but no reliable, simple and simply-operated hand-held filtering device is available that can produce hemolysis-free serum or plasma.

Prior art in the general field include U.S. Pat. Nos. 2,460,641; 3,814,258; 4,343,705; 4,477,575; 4,540,492; 4,828,716; 4,883,068; 4,906,375; 4,960,130; 5,030,341; 5,181,940; 5,308,508; 5,364,533; 5,413,246; 5,471,994; 5,555,920; 5,681,529; 5,683,355; 5,759,866; 5,876,605; 5,919,356; 5,979,669; 5,996,811; 6,045,699; 6,170,671; 6,261,721; 6,225,130; 6,406,671; 6,410,334; 6,465,256; 6,471,069; 6,479,298; 6,497,325; 6,506,167; 6,516,953; 6,537,503; 6,659,288; 6,659,975; 6,755,802; 6,803,022; 6,821,789; 7,070,721; 7,153,477; 7,767,466; 7,744,820; 7,927,810; and 7,993,847; and US 2010/0093551.

It is recognized to be desirable to work quickly and efficiently with blood samples of the order of 1 milliliter volume. Most protein analyzers for instance require 10 to 100 micro-liters per test and it is common to employ 10 or so tests. Multiplexed biomarker cassettes, e.g. those employing micro arrays, typically run 8 to 12 assays simultaneously, and call for less than 100 micro-liter of serum or plasma for the set of assays.

Devices and techniques made possible by the present disclosure can simply, inexpensively and rapidly meet the need for obtaining suitable blood serum and other blood-derived fluids from small volume whole blood samples. Neither centrifuge separation nor other inconvenient techniques are employed, while sterile separation at point of collection or point of patient treatment can be achieved.

The level of hemolysis, the presence of hemoglobin within the plasma or serum as a result of cell damage, may not interfere with most diagnostic tests and specifically most protein or ELISA tests, but excess hemolysis could be indicative of patient health conditions that would need to be considered, and consequently lead to an erroneous diagnosis. More specifically the presence of hemoglobin in serum may yield erroneous reading of the blood potassium concentration. For these reasons desirable hemolysis quantifications of low value have been established.

Consequently, in order to be practical, a plasma or serum extraction processor device needs to keep damage to red cells to a minimum.

It is important to consider further that the venous puncture commonly causes some red cells breakage so that the standards that have been established to define levels of acceptable hemolysis leave little room for additional hemolysis by serum separation features. This is where previous devices have failed to meet exacting standards.

U.S. Pat. No. 4,477,575 teaches the use of glass fibers with diameter from 1 to 4 micron can be efficiently used to separate cells from plasma or serum in a depressurization syringe-like device. The use of this type of glass fiber has been adopted in later processes as well as the suction/depressurization serum extraction method, as exemplified by U.S. Pat. No. 5,364,533 that employs pre-evacuation of a device.

Later prior art as exemplified in U.S. Pat. Nos. 7,744,820, 7,927,810 and 7,993,847 and US 2007/0082370 describe blood collection and serum separation using a an internal negative pressure plurality of interconnected tubes as well as the use of glass fibers as filter medium. This prior art attempts to control hemolysis by stratification of filtration porosity using a membrane with a void ratio under 30% and/or altered retention properties of the filtration column media.

U.S. Pat. No. 5,876,605 similarly uses glass fiber and seeks to minimize hemolysis with suitable mixing of the blood with an aqueous solution.

U.S. Pat. Nos. 5,979,669, 5,996,811, 6,045,699 and 6,170,671 also use glass fiber as a filtrate material and incorporate means to regulate outflow of filtrate in order to accommodate variation in hematocrit and control hemolysis. They all show how a number of interconnected tubular devices create a pressure difference by connection to a suction pump or device. Typically the final outlet filter membrane is constructed to regulate serum outlet flow.

U.S. Pat. No. 5,979,669 teaches "In another aspect of the blood filter unit of the invention, a flow area-regulating member is provided on the blood filtering material on the filtrate outlet side which is, in general, the microporous membrane. The flow area-regulating member is made of liquid-impermeable material, and has an opening having an area smaller than the blood filtering material thereby regulates so that filtrate flows out through the opening. A suitable area of the opening is about 20 to 90%, preferably about 50 to 90% of the blood filtering material area on the filtrate outlet side."

"The flow area-regulating member can be made by various commercial adhesive tapes, plastic film, thin plastic sheet or the like, and adhesive may be applied to the adhering face of the blood filtering material."

U.S. Pat. Nos. 5,364,533 and 5,979,669 teach the use of a number of interconnected and detachable successions of tubes to create a pressure difference across a filter assembly in order to obtain plasma by filtration.

U.S. Pat. Nos. 6,506,167, 6,659,288 and 6,045,699 suggest the use of stratified filtration column as well as external active sequencing of controlled differential pressure forcing the blood through the filter column or the entire device from blood inlet to filtrate outlet.

U.S. Pat. No. 6,045,699 teaches that a suitably hemolysis-free filter device can be constructed where pressure differential across a filter assembly of an evacuated device is actively controlled from a tethered pressure source external to the filter device. It teaches to sequence the pressure differential with a pressure sequencer where filtration begins with a low pressure differential which is "controllably increased" as filtration progresses. The patent teaches using active external equipment such as a peristaltic pump or a syringe. It teaches to "trace" pressure different variation with time and to "adjust suction or pressurizing speed."

U.S. Pat. No. 7,993,847 teaches the use of filter assembly in which a membrane exit filter, in a passive warmer, regulates the pressure differential across a filter assembly, seeking to yield a substantially hemolysis-free serum sample.

The membrane exit filter has a number of micron size apertures. But such a membrane is totally ineffective to limit the flow of air across it as air molecules are sub angstrom in dimensions. Such a membrane is effective only to limit liquid flow and have any effect much later in the filtration process when blood has already reached and serum or plasma has already traveled through the filter assembly. Such a device starts the filtration process with maximum pressure differential across the filter assembly and is insufficient to control hemolysis to the low level necessary.

A prior attempt by one of us to meet the present need is shown in US2010/0093551. It has the requirement of repeated hand movements and other drawbacks, and lacks the critical flow rate or pressure differential-limiting element or device geometry now to be described. Like many other attempts to meet the need, has not been commercialized.

SUMMARY

The present invention teaches how to make a totally independent filter device with few parts able to induce controlled pressure differential conditions that permits delivery of suitably hemolysis free serum or plasma from blood. The blood may be undiluted whole blood that is simultaneously drawn from a subject. The blood may be sourced from another vessel.

The subject of this invention is to offer a blood filtration method to obtain serum that accommodates hematocrit variations and delivers an acceptable level of hemolysis. This invention contrasts in two ways with prior art. First this invention teaches how to minimize hemolysis by passive control of the pressure differential forced upon the blood through the filter assembly. Second this invention teaches how to control in a passive way the pressure differential forced upon the blood through the filter assembly by controlling the inflow rate of blood prior to contact with the filter assembly.

In addition this invention in contrast with prior art, teaches how to build such a filter device using a single tube, therefore minimizing manufacturing costs.

Another aspect of this invention is to offer a method of extracting by filtration a volume of serum from blood with a minimum of hemolysis.

This invention teaches how to sequence in a totally passive manner the pressure differential across the filter assembly of an evacuated device and yield substantially hemolysis-free serum. As blood is introduced into the device the filtration is caused to proceed with only a slowly rising pressure differential followed with a very slowly declining pressure differential and termination of the process. This invention teaches in a passive manner the control of the pressure differential across a filter assembly in an evacuated device through the control of the blood intake flow rate. The control of the pressure differential takes effect as the blood enters the device in contrast to the teaching of U.S. Pat. No. 7,993,847 where control begins much later and only after a quantity of blood has reached and plasma or serum has traveled through the entire filter assembly.

Another aspect of this invention is a mechanically simple method to passively control the magnitude of the pressure differential across both ends of an evacuated hand-held tube-like device separated by a filter element as blood enters one end as shown on FIGS. 1A and 1B.

Another aspect of this invention is a mechanically simple method to passively control the rate of change of the pressure differential across both ends of an evacuated hand-held tube-like device separated by a filter element as blood enters one end as shown on FIGS. 1A and 1B.

Another aspect of this invention is a mechanically simple method to passively control the magnitude of the pressure differential across both ends of an evacuated hand-held tube-like device separated by a filter element by controlling the rate of entry of the blood into the device as shown on FIG. 1A.

Another aspect of this invention is a mechanically simple method to passively control the rate of change of the pressure differential across both ends of an evacuated hand-held tube-like device separated by a filter element by controlling the rate of entry of the blood into the device as shown on FIG. 1A.

Another aspect of this invention is an evacuated hand-held tube-like device holding in its central region a filter element and a flow rate controlling element constructed such that as blood enters the device via the flow rate controlling element the magnitude of the pressure differential across the filter element is controlled by the flow rate control element as shown on FIG. 1B.

Another aspect of this invention is an evacuated hand-held tube-like device holding in its central region a filter element and a flow rate controlling element constructed such that as blood enters the device via the flow rate controlling element the rate of change of the pressure differential across the filter element is controlled by the flow rate control element as shown on FIG. 1B.

The device is intended to be used instead of a common pre-evacuated blood collection device such as a BD Vacutainer™ and can deliver serum or plasma by filtration directly without use of a centrifuge. It incorporates a flow rate control section preceding the filter, which may be internal to the evacuated tube or external. Blood is drawn into the partially evacuated device and with appropriate flow rate traverses to and through a filter assembly that captures cells but permits serum or plasma to flow through into a collection chamber.

The device enables simple and rapid extraction of blood serum or plasma in milliliter quantities from a collected blood sample. The device can also provide for the addition of an agent that may coat the filter or the tube. Syringe extraction of blood serum from the device can be achieved via an access septum located at the downstream end of the collection tube. The device permits all functions to be performed rapidly, without exposure of personnel to needles, and with minimum danger of exposure of the operator to the sample or contamination of the sample while enabling standard evacuated collection tube methods to be used.

In preferred implementations, the invention is a blood separation device in the form of a cylindrical tubular assembly similar in shape to a 6 ml Vacutainer™ It incorporates an input flow rate control element and from a drawn blood sample somewhat smaller than 2 milliliter produces approximately a 0.25 milliliter volume of blood serum practically free of hemoglobin.

In some preferred implementations the input flow rate control element may be internal to the tube-like device.

In other preferred implementations the input flow rate control element may be external to the tube-like device.

In some preferred implementations the invention incorporates, within the blood input chamber, an elastically compressible element such as a closed cell member of resilient plastic or rubber foam or an air-filled bladder that regulates the rate of evolution of the pressure difference across the filter assembly as blood enters the region of the compressible element.

Preferably, neither air nor gas is permitted to enter any part of the device until the filtration process has been completed and the serum chamber has been brought to atmospheric pressure by letting air at atmospheric pressure enter through the serum access septum or through an equivalent port. That process takes approximately 1 or 2 minutes.

Another aspect of this invention is a mechanically simple method to passively control the magnitude of the pressure differential across both ends of pressurized hand-held tube-like device separated by a filter element as blood enters one end as shown on FIGS. 1D and 1E.

Another aspect of this invention is a mechanically simple method to passively control the rate of change of the pressure differential across both ends of an evacuated hand-held tube-like device separated by a filter element as blood enters one end as shown on FIGS. 1D and 1E.

Another aspect of this invention is a mechanically simple method to passively control the magnitude of the pressure differential across both ends of a pressurized hand-held tube-like device separated by a filter element by controlling the rate of entry of the blood into the device as shown on FIG. 1C.

Another aspect of this invention is a mechanically simple method to passively control the rate of change of the pressure differential across both ends of a pressurized hand-held tube-like device separated by a filter element by controlling the rate of entry of the blood into the device as shown on FIG. 1C.

The independent blood filter device depends on flow geometry to deliver blood serum or plasma free of detrimental levels of hemoglobin. It depends critically on an upstream flow rate or pressure differential limiting control element or device that limits the rate of change of pressure differential across the filter element. Pre-evacuated versions can be used to simultaneously draw blood from a living being and provide pressure differential across the filter element between an evacuated collector and a supply end open to atmosphere. A unit can be pressurized by hand motion employing the external shape of a partially filled blood collection tube as a piston to produce pressure in advance of the control element or device to create the pressure differential across the filter element to a collector vented to atmosphere. The control element or device is disclosed in numerous forms, including specially sized flow constrictions and compliant arrangements.

The features described in the preceding pages are comprehended in the following summary:

In a first aspect, the invention features a filtering device for filtering blood to obtain serum or plasma in a container, the container having access at both ends, a filter located within the container, and a flow rate or pressure differential limiting control element or device, the limiting element or device located upstream of the filter.

Preferred implementations of this aspect of the invention may incorporate one or more of the following:

The container may be partially evacuated. The limiting control element or device may be located outside the container. The limiting control element or device may be integral with a blood drawing needle assembly. The filtering device may be fitted with an entering flow rate limiting control element or device. The container during operation may be partially pressurized. The limiting control element or device may be located inside the container. The limiting control element or device may be a flow constriction element or device. The flow constriction element or device may be in the form of a pin hole or pin holes in a flow-blocking disk. The flow constriction element or device may be in the form of or may comprise a selected length of capillary tubing. The flow constriction element or device may be in the form of or may comprise a fine mesh or porous foam. The flow constriction element or device may be in the form of or may comprise a passage defined by a screw like segment. The filtering device may have a limiting control element or device constructed to limit differential pressure across blood in the inlet side of the filter. The filtering device may have a limiting control element or device preceding the filter that limits entering flow-rate of whole blood. The filtering device may have a limiting control element or device preceding the filter that defines entering pressure increase rate in whole blood. The filtering device may be portable or hand held, and may include a volume sized for blood drawn from a living being. The material of the filter may comprise glass microfibers and micro-porous membrane on a locating support. The container may be a tube. The filtering device may have an access septum at the inlet end of the container or tube. The filtering device may have an access septum at the outlet end of the container or tube. The filtering device may have, at the outlet end of the container or tube, a removable element in the form of an end-plug with a serum or plasma holding cavity. The filtering device may include a volume pre-evacuated for drawing blood from a source. The volume may be pre-evacuated for drawing blood from a living being. The filtering device may be constructed for controlling the incoming blood flow rate into a container or tube holding a filter in its central region such that the rate of increase of the pressure differential between the two sides of the filter stays below 30 mmHg per second. The filtering device may be constructed to limit rate of increase to stay below 20 mmHG per second. The filtering device may be constructed, by the axial position of the filter in the container or tube, for controlling the rate of increase of the pressure differential between the sides of the filter to stay below 30 mmHg per second. The filtering device may be constructed to limit rate of increase of pressure differential to stay below 20 mmHg per second. The filtering device may be pre-evacuated to induce flow of whole blood into the device, and may be constructed to define incoming blood flow rate into the volume at the inlet side of the filter to increase the pressure differential across the filter at a rate below 30 mmHg per second. The filtering device may be constructed to limit rate of increase of pressure differential to stay below 20 mmHg per second. The container may be a tube and the pressure differential may be between the ends of the tube. The limiting control element or device may be an insertion of a compressible closed cell volume. The filtering device, following blood collection, may be constructed to be-pressurized by manual action of the user to produce pressure on collected blood to force the blood through the control element or device, and through the filter, to a vented collector. The filtering device may be adapted for use with a first tubular member which is a pre-evacuated blood collection member, and the device may comprise a member pre-fitted in shape to receive the first tubular member and to be moved relative to the first tubular member to produce positive pressure, preceding an internal whole blood flow constriction element.

The pressure differential across the filter may be limited to below 30 mmHg per second. The pressure differential across the filter may be limited to below 20 mmHg per second. The flow rate through the filter may be approximately 2 to 10 cc per minute. The flow rate may be between 3 to 6 cc per minute. The device may be constructed to produce a volume of between about 1 to 2 cc filtrate. The device may be constructed to produce a volume of about 1.5 cc filtrate. The limiting control element or device may be a tubular element between ½ inch and 4 Inches in length and may have an internal diameter between about 0.008 and 0.013 inch.

In another aspect, the invention comprises a method of obtaining blood serum or plasma using the filtering device according to the first aspect described alone or together with any of the further features mentioned.

The major benefits offered by the devices are:
Cost saving
Simplicity of operation
Under three minute plasma delivery
Serum availability at the point of care
Protection of the operator from exposure
Freedom of contamination of the sample
Elimination of the need for a centrifuge The details of one or more embodiments of the invention are set forth in the accompanying drawings and the description below. Other features, objects, and advantages of the invention will be apparent from the description and drawings, and from the claims.

In FIGS. 1-6 the geometry of a flow rate or pressure differential limiting control element or device upstream of the filter is used to define conditions with pre-evacuated tubes. The tubes may be blood collection tubes. In FIGS. 7-9 the geometry is used in respect of a pressurized system.

DESCRIPTION OF DRAWINGS

FIG. 1 illustrates prior art;
FIG. 1A diagrammatically indicates the flows of devices according to present invention having a flow regulator upstream of a pre-evacuated collection device containing a filter assembly, the device shown having a tubular housing;
FIG. 1B similar to FIG. 1A, indicates the flows of devices having a flow or pressure regulator within a pre-evacuated collection device, upstream of a filter assembly within the device, the device shown having a tubular housing.

FIG. 3 is a photograph of a blood collection and flow regulator assembly and separate insertion guide for use with a device according to FIG. 1A, while

FIGS. 5 and 6 are pressure vs. time plots of the pressures within a pre-evacuated blood collection device with internal filter assembly respectively with no flow control, and the flow control of the device according to FIG. 1A employing the flow regulator of FIG. 3A;

FIG. 7 is a longitudinal cross-section of a filter device assembly and a collection tube holding blood in position to be inserted into the filter device, here the collection tube shown is fitted with an access septum;

Like reference symbols in the various drawings indicate like elements.

DETAILED DESCRIPTION

Figure 1D:
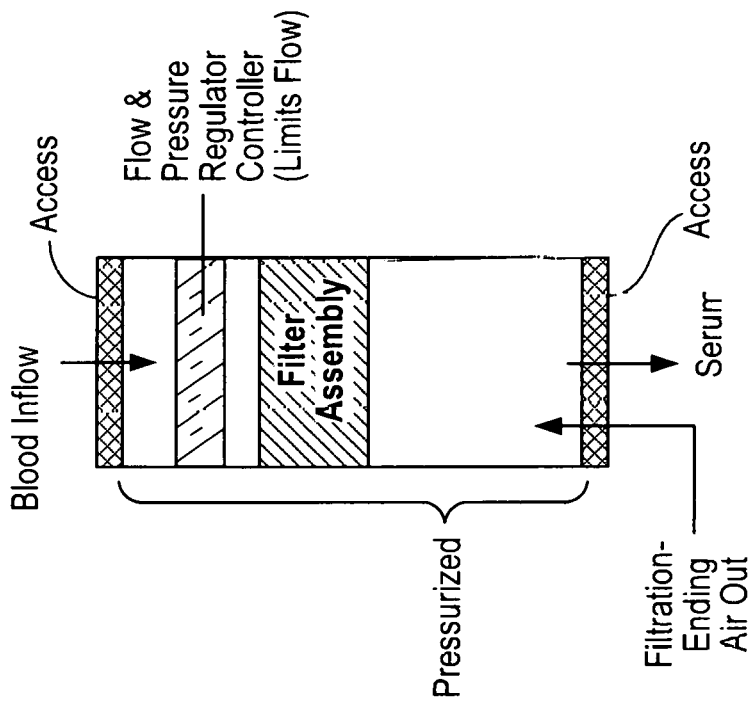
FIG. 1D similar to FIG. 1C, indicates the flows of devices having a flow or pressure regulator within a pressurized collection device, upstream of a filter assembly within the device, the device shown having a tubular housing
Figure 1C:
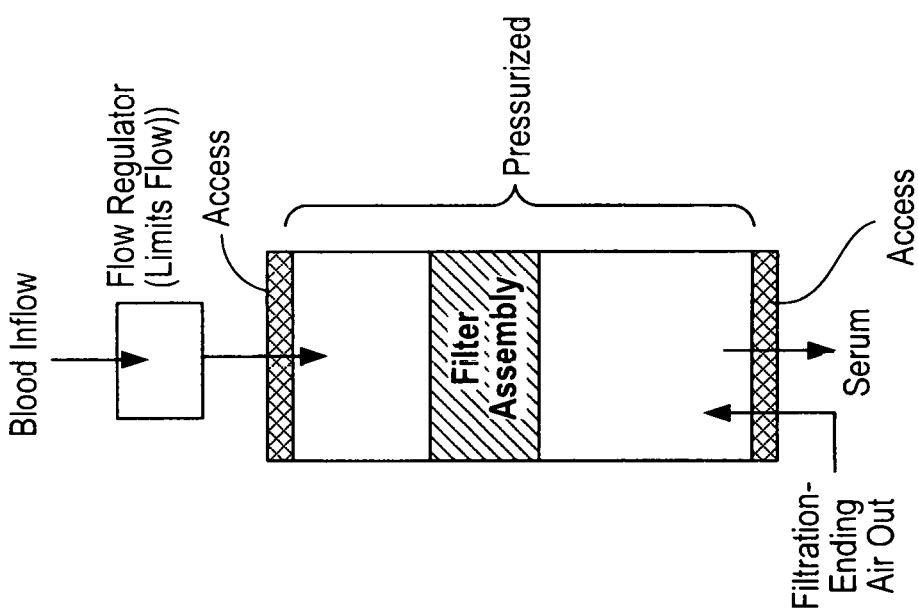
FIG. 1C diagrammatically indicates the flows of devices according to present invention having a flow regulator upstream of a pressurized collection device containing a filter assembly, the device shown having a tubular housing.

In the presently preferred implementation the device comprises a tube-shaped assembly closed at each end with a needle-penetrable access septum. The blood inlet access septum located at one end of the tube connects for inlet of blood to the blood holding chamber and the outlet access septum located at the other end of the tube faces the serum/plasma collection chamber and can function as the air inlet port to terminate the filtration process. A filter assembly is fixed in place in the central region of the tube. A passive blood flow controlling segment may be located between the blood inlet access septum and the filter assembly (FIG. 1B) or may be external, preceding the device (FIG. 1A). FIGS. 1A and 1B illustrate flow geometries based on pre-evacuation of container or tubes. Preferred implementations are shown in FIGS. 2-6. FIGS. 1C and 1D illustrate similar flow geometries based on pressurization of the container or tube, similar preferred implementations of which are shown in FIGS. 1-9.

The inlet access septum is adapted for being pierced by a standard blood-collection needle assembly (needle penetrable) and defines one end of the chamber free to accept the blood sample for filtration. A flow rate regulating segment adjacent to this access septum regulates the rate of flow of blood approaching the filter assembly and defines the pressure differential driving the filtration process in the pre-evacuated unit. The filter assembly is preferably designed to cover the entire cross-section area of the tube. The filter assembly captures the cellular components of the blood and permits passage of the serum or plasma components. The filter assembly preferably terminates with a peripherally sealed element that prevents flow-around (bypass flow) of blood product and an axial retainer pressed or molded into place.

The axial location of the filter assembly and starting point pressure (vacuum) level of the pre-evacuated device can be used to coordinate the pressure differential changes across the filter assembly.

Figure 2:
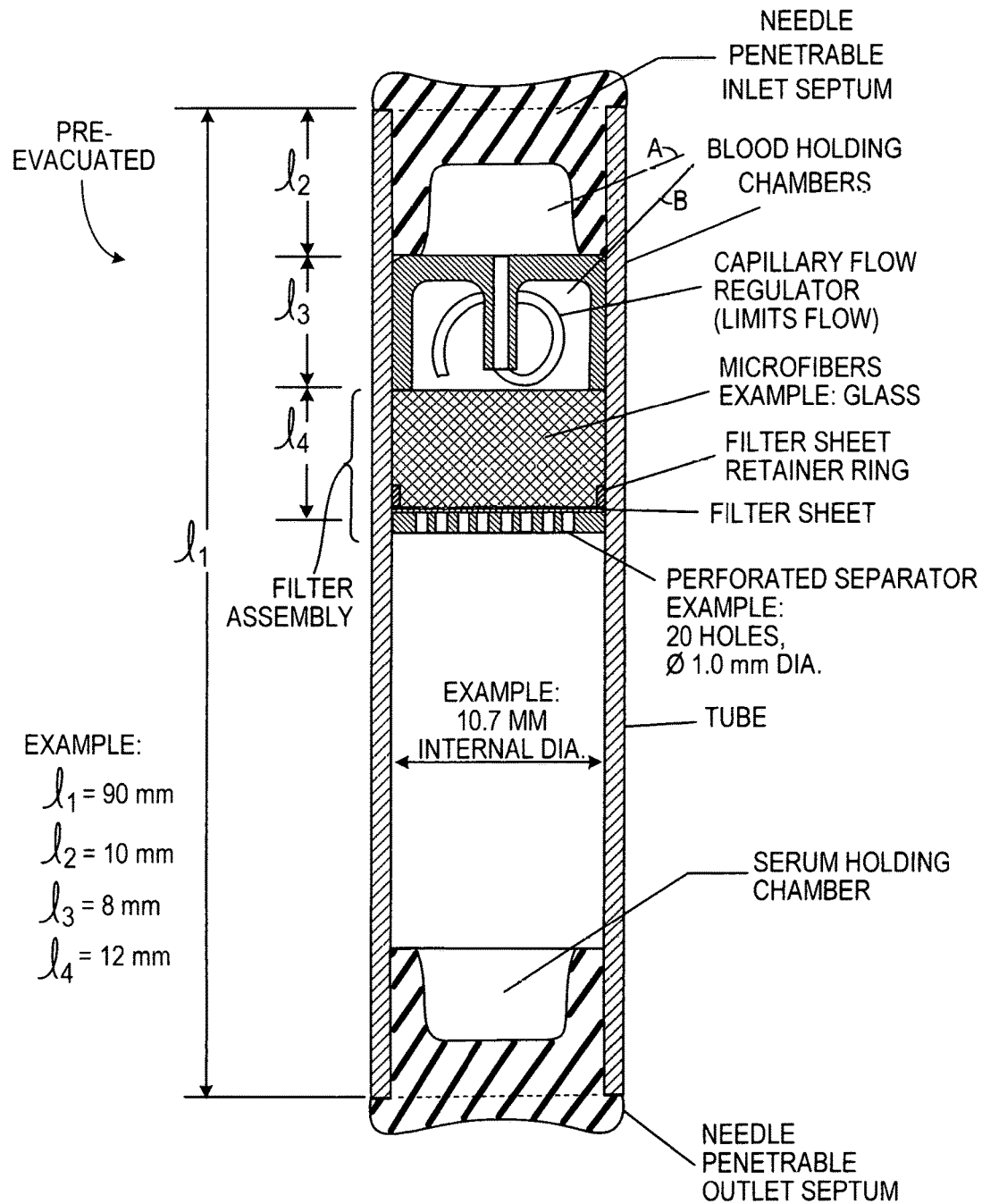
FIG. 2 is an implementation of the device generically illustrated in FIG. 1B, the device having a capillary flow regulator between first (A) and second (B) blood holding chambers upstream of the filter assembly within a tubular housing and a needle-penetrable access septum at the end of the tube for serum or plasma.
Figure 2A:
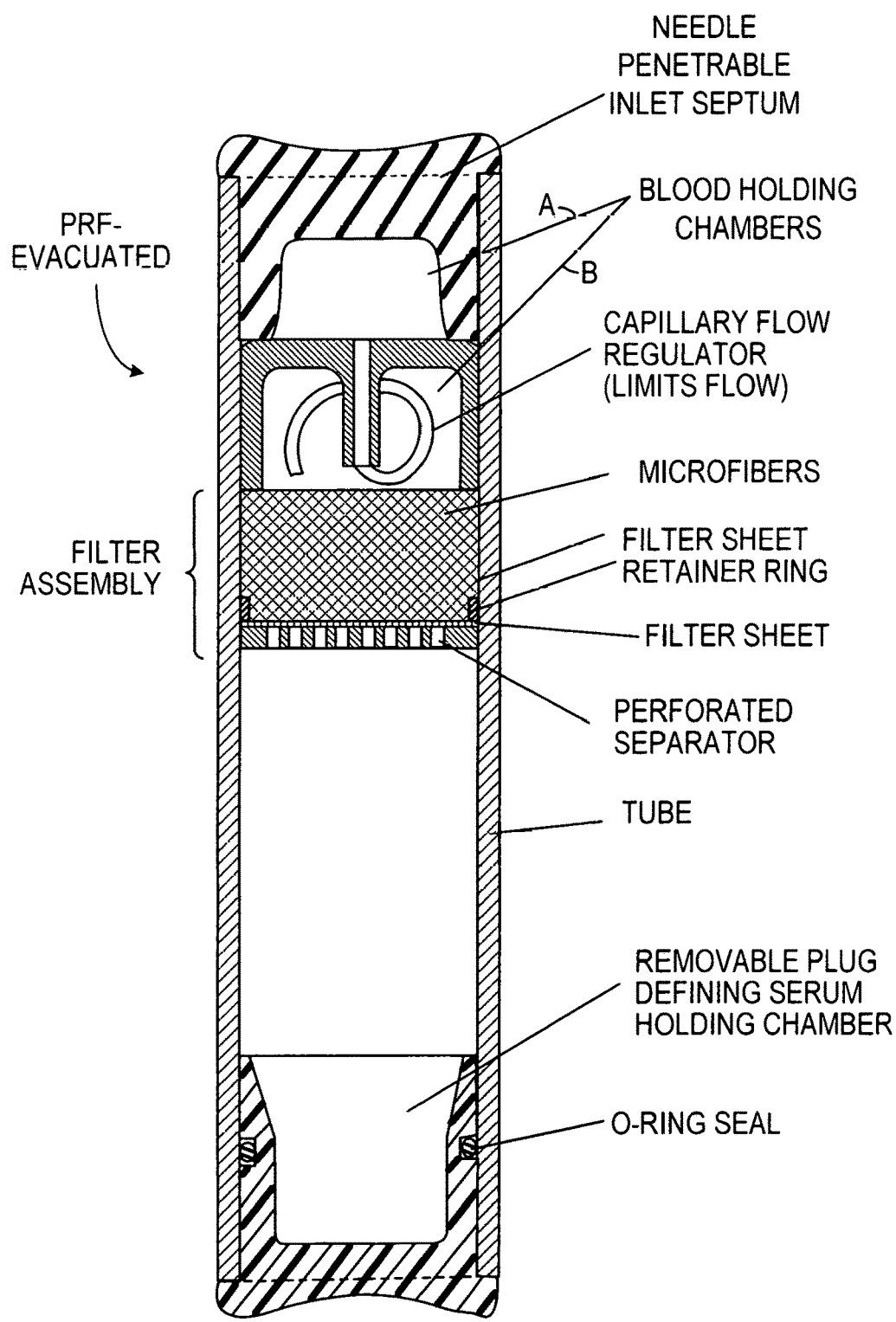
FIG. 2A is an implementation of the device generically illustrated in FIG. 1B, the device having a capillary flow regulator between first (A) and second (B) blood holding chambers upstream of the filter assembly within a tubular housing and a sealed but removable slide-fit end plug that defines a holding chamber for serum or plasma.
Figure 2B:
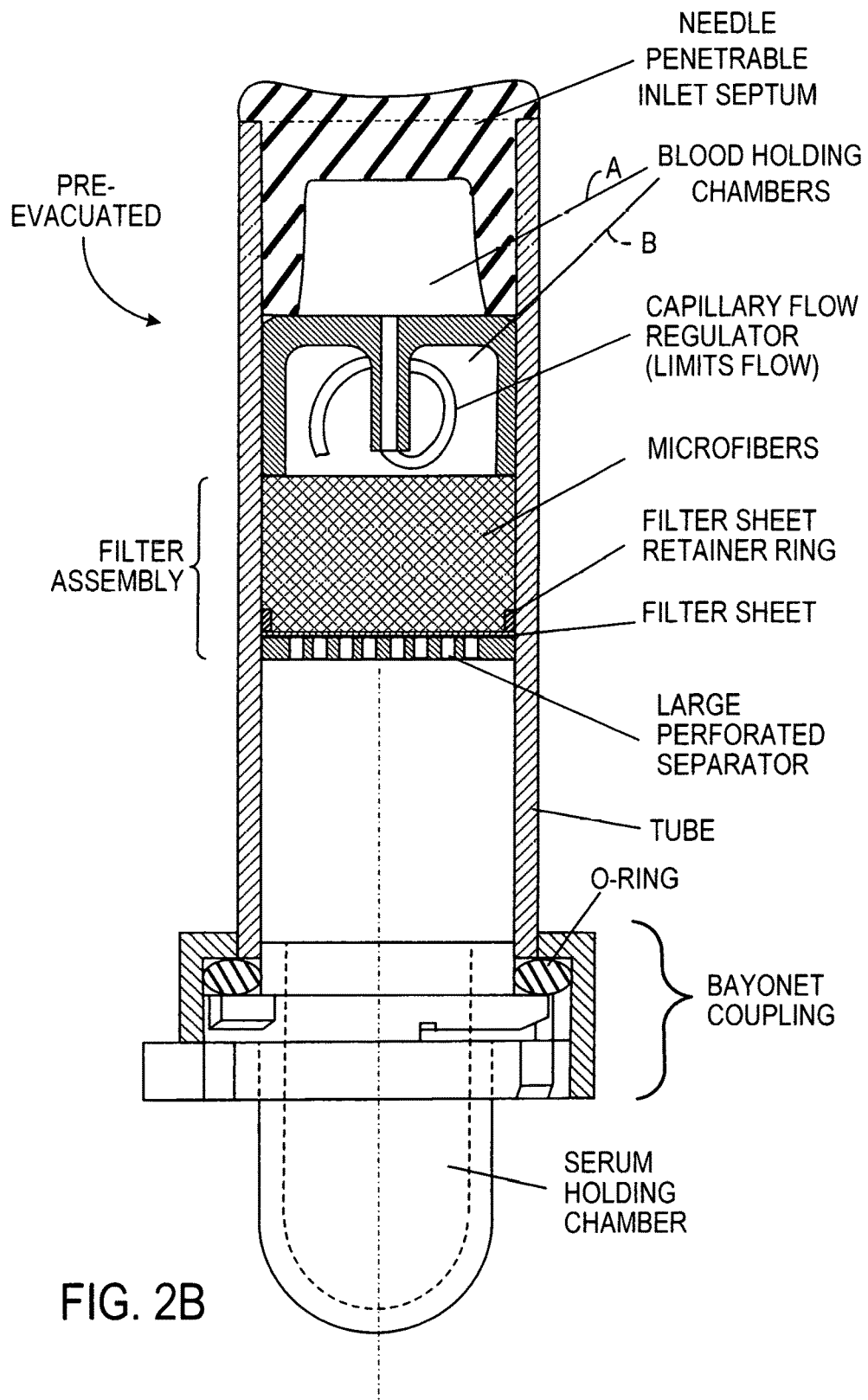
FIG. 2B is an implementation of the device generically illustrated in FIG. 1B, the device having a capillary flow regulator between first (A) and second (B) blood holding chambers upstream of the filter assembly and a sealed but removable end holding chamber for serum or plasma, that is sealed and held to the tubular housing by a bayonet coupling device.
Figure 2C:
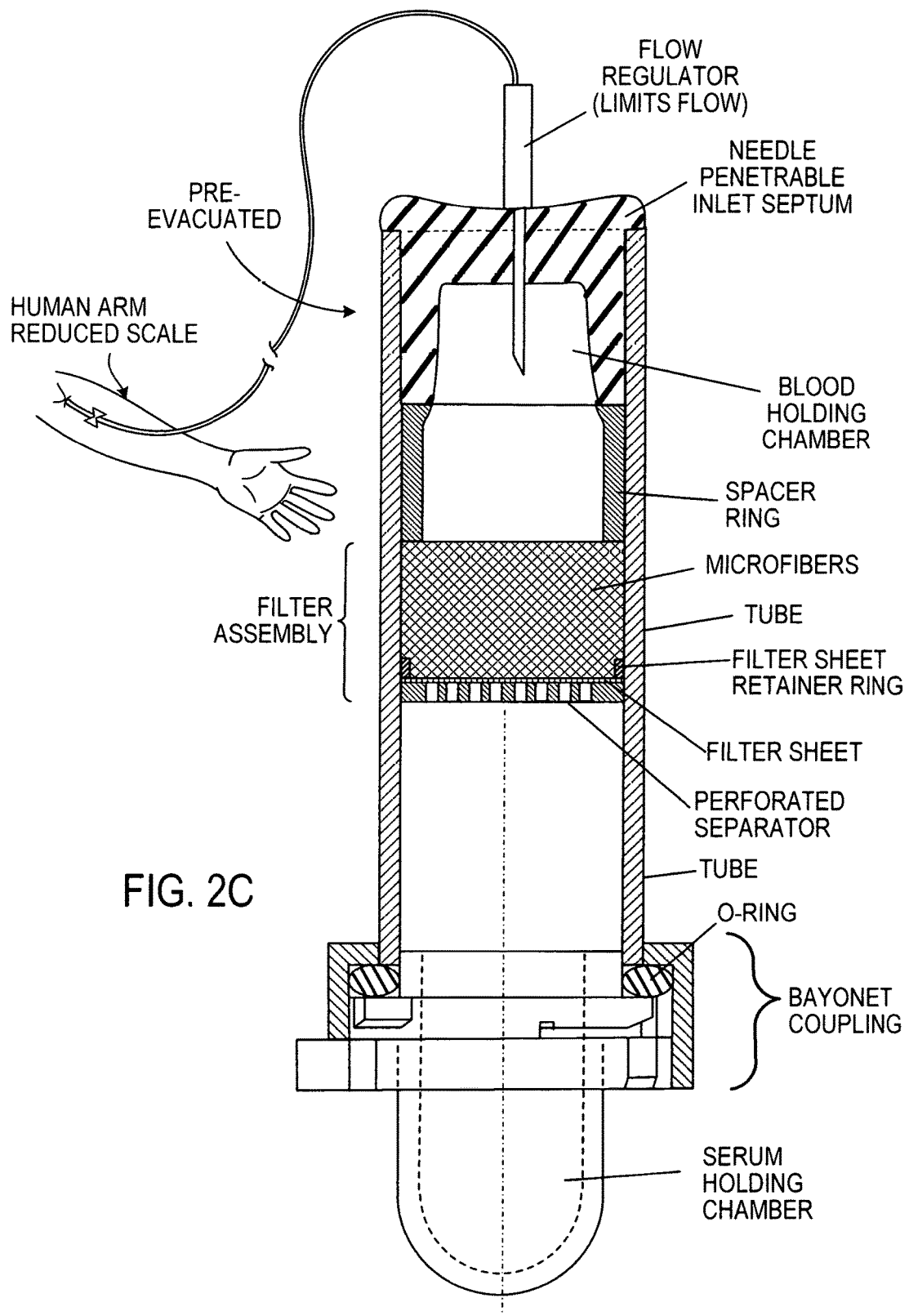
FIG. 2C is an implementation of the device generically illustrated in FIG. 1A, the device having a flow regulator upstream of the entry to a blood holding chamber preceding the filter assembly and a sealed but removable end holding chamber for blood serum or plasma, that is sealed and held to the tubular housing by a bayonet coupling device, the figure further illustrating the arm of a human subject (reduced scale) and usual blood collection needle and connection tubing for conducting blood from the subject.
Figure 2D:
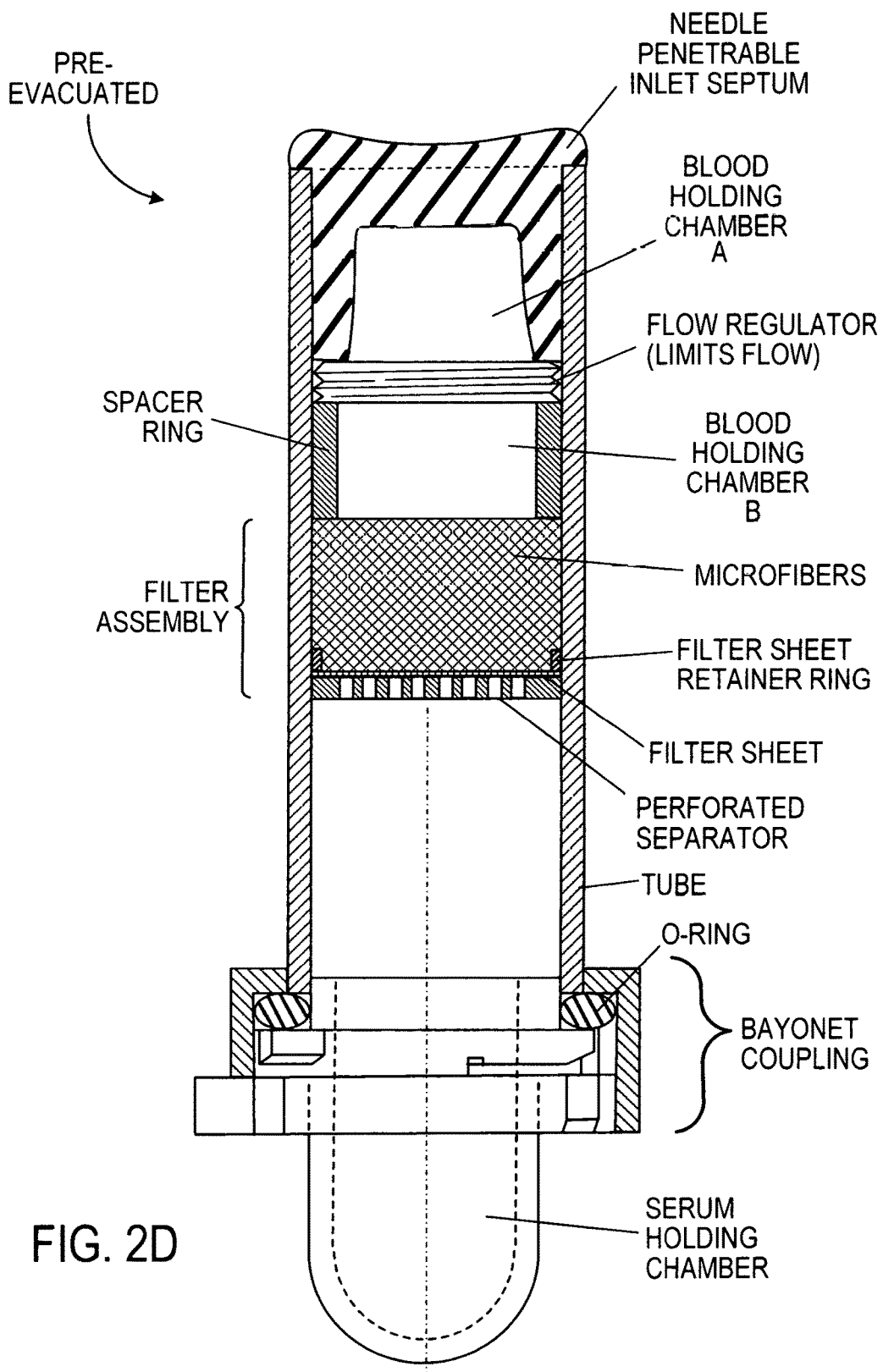
FIG. 2D is an implementation of the device generically illustrated in FIG. 1B, the device having a flow regulator in the form of a narrow screw-thread-defined helical passage, between first (A) and second (B) inlet holding chambers upstream of the filter assembly and a sealed but removable end holding chamber for serum or plasma, that is sealed and held to the tubular housing by a bayonet coupling device.
Figure 2E:
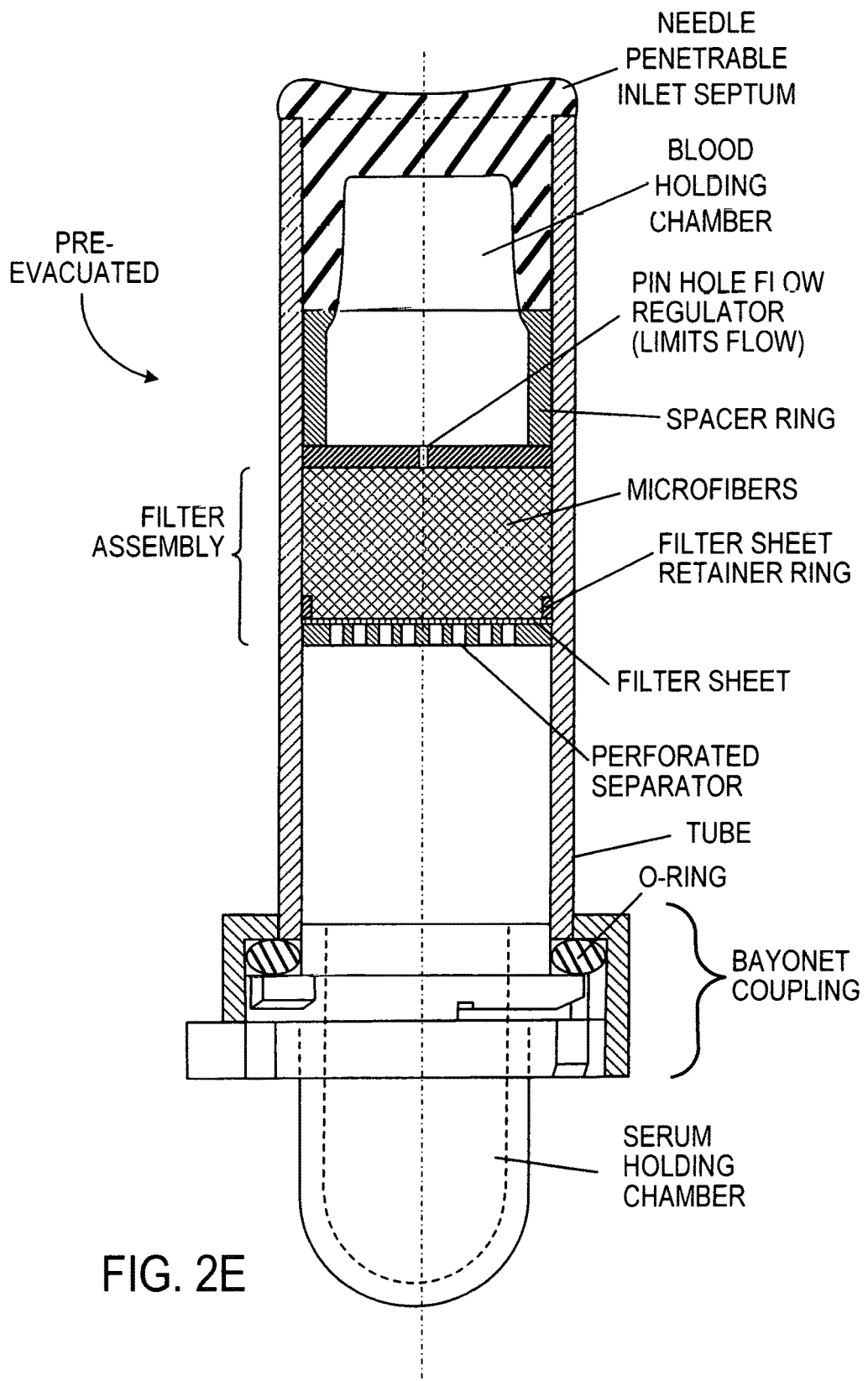
FIG. 2E is an implementation of the device generically illustrated in FIG. 1B, the device having a pin hole flow regulator passage between a blood holding chamber upstream of the filter assembly and a sealed, but removable, end holding chamber for serum or plasma, that is sealed and held to the tubular housing by a bayonet coupling device.
Figure 2F:
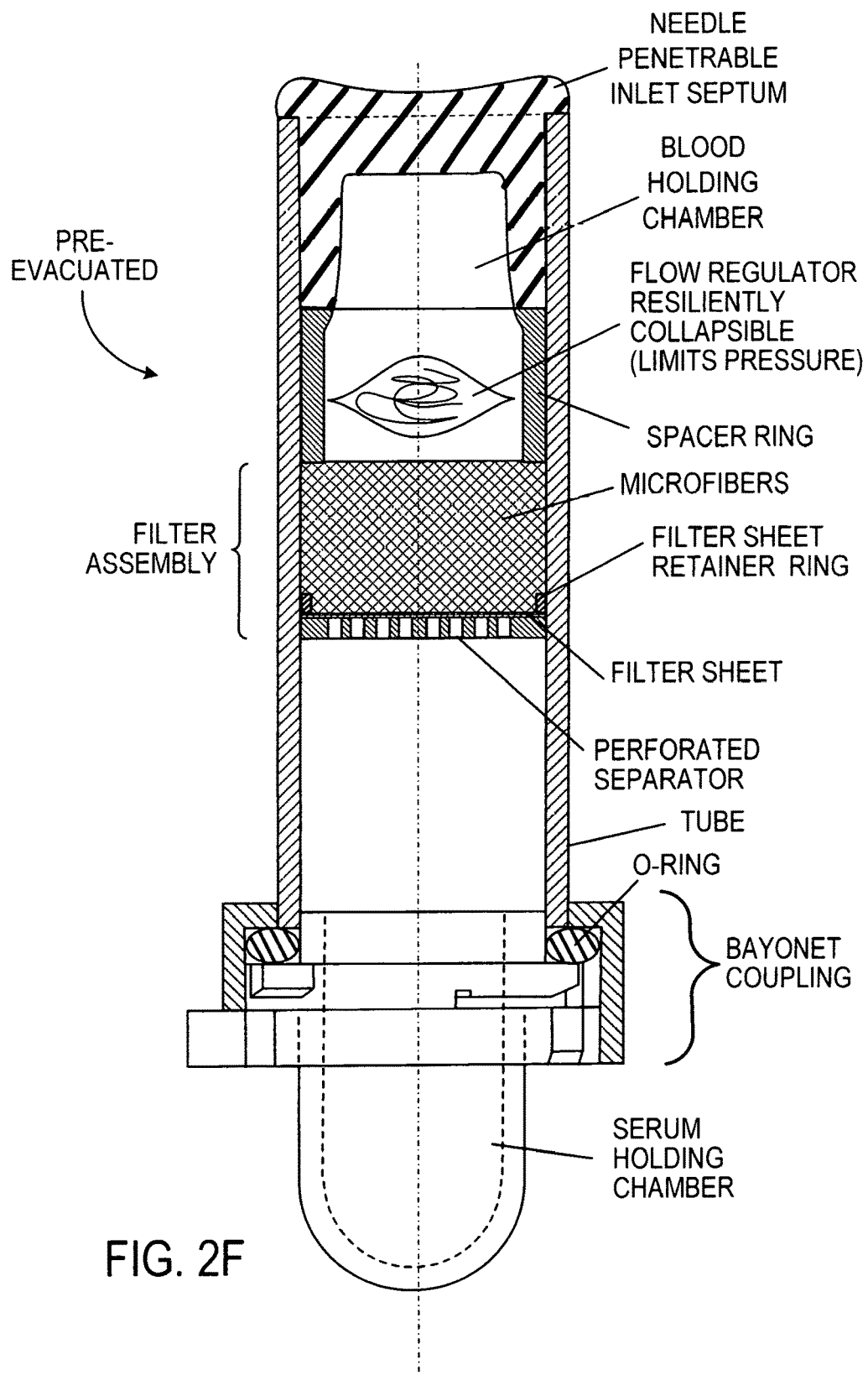
FIG. 2F is an implementation of the device generically illustrated in FIG. 1B, the device having a resiliently collapsible flow regulator (e.g. air-filled bladder or mass of collapsible rubber-like foam) bladder within an inlet blood holding chamber upstream of the filter assembly and a sealed, but removable, end holding chamber for serum or plasma, that is sealed and held to the tubular housing by a bayonet coupling device.

A volume of elastomeric compressible media or a resiliently collapsible element may be located in the chamber free to accept the blood sample as shown on FIG. 2F for modulating the pressure differential. Preferably closed cell silicone sponge or foam made of natural rubber, or Nitrile, with durometer less than Shore 45 may be used, or a partially air-filled bladder, for instance.

The terminal end of the tube forms the low pressure chamber that induces the filtration process and is the serum collection chamber. It is closed with a second access septum through which atmospheric air can be caused to enter to equilibrate pressure across the filter assembly to terminate filtration, and for subsequent removal of filtered material via a needle and syringe.

In its presently preferred implementations shown on FIG. 2 the serum collection access septum has a hollow space sized to hold all the filtrate and can be slide-ably removed from the tube for serum aspiration with a pipette.

In another implementation the scrum collection closure segment can be rigid and held in place with a simple pressed in O ring as shown on FIG. 2A or be detachable via a bayonet connector as shown on FIG. 2B to implement depressurization and access to the filtrate.

In preferred implementations a region adjacent to the blood inlet access septum of the tube is dedicated to hold the blood sample to be filtered until filtration has been performed and to retain all extraneous blood and blood components, liquid and gaseous.

One aspect of the invention is the incorporation of an intake blood flow rate controller/regulator prior to the filtration stage, FIG. 1A. In certain preferred embodiments the controller/regulator of the rate of blood flows is located within the device, FIG. 1B.

Figure 4:
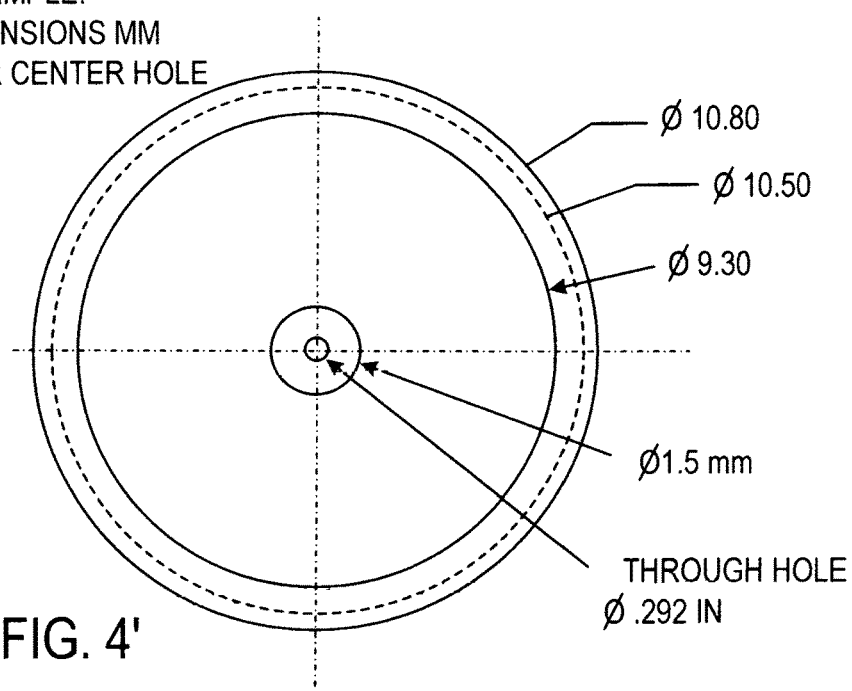
FIG. 4 is a side cross-section view and FIG. 4' a top view of an implementation of a cup-shaped holder for the capillary flow regulator element useful in implementations according to FIGS. 2, 2A, and 2B.
Figure 4:
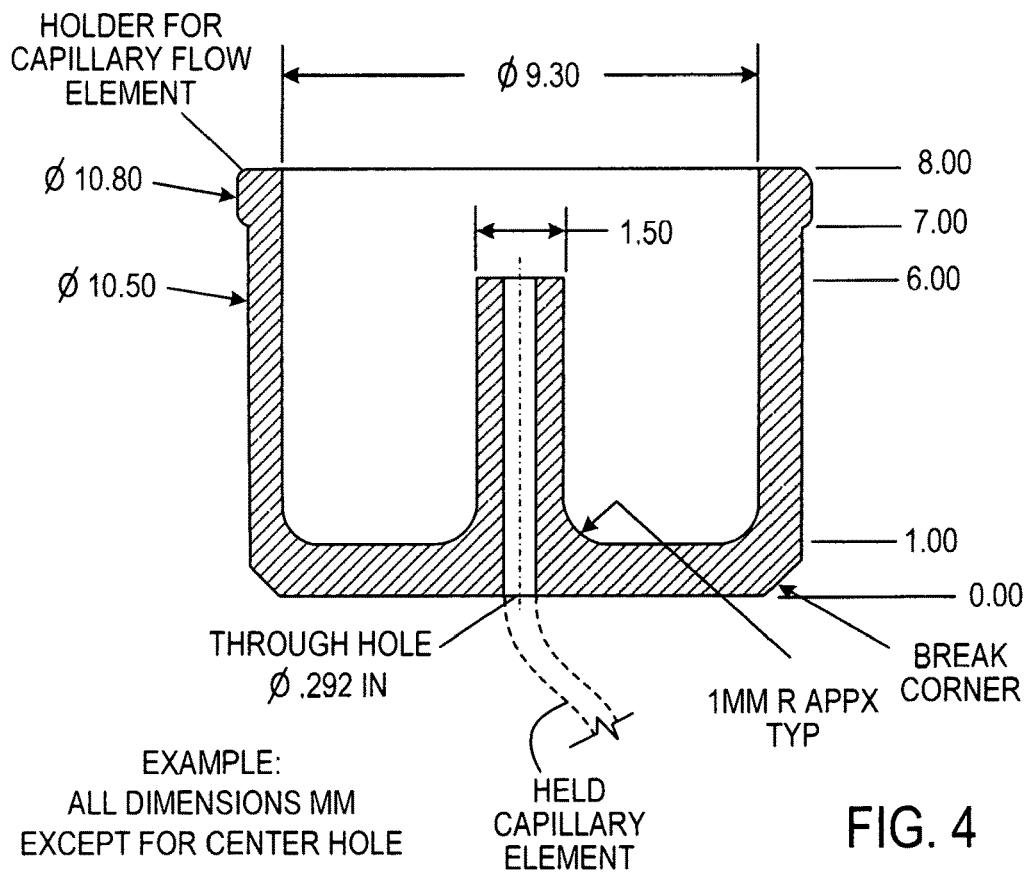
Figure 4A:
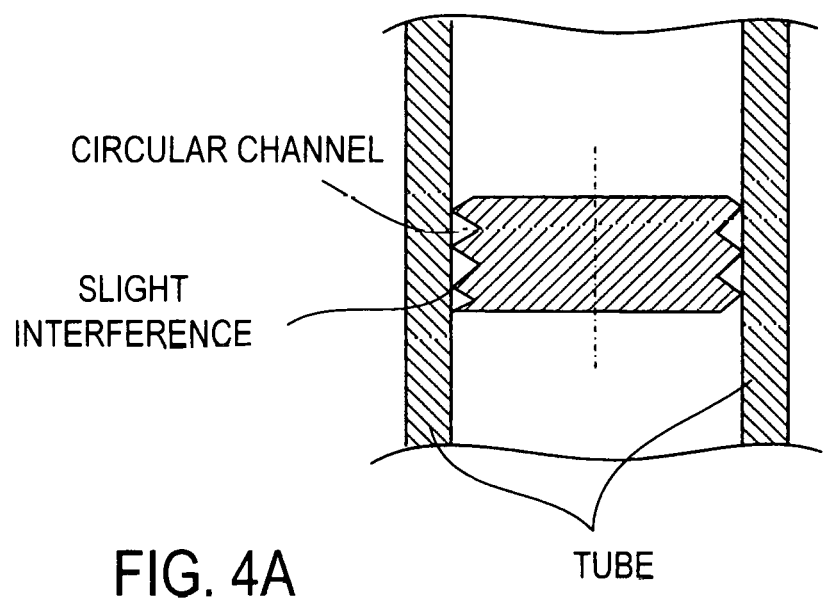
FIG. 4A is a side cross-section of a helical path flow regulator (constrictor) formed by a screw thread inside the tubular housing of the device of FIG. 2D while FIG. 4A' is a side view of the screw-thread-defining element.
Figure 4A:
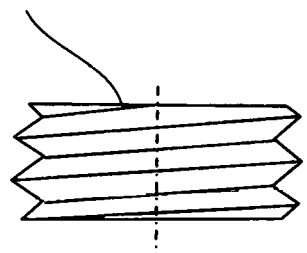

In certain preferred embodiments the flow rate controller/regulator limits the rate of blood flow that can enter the filter assembly. FIG. 2 and FIG. 4b In another embodiment the controller/regulator/restrictor is located between the access septum and the filter assembly as shown on FIG. 2D; FIGS. 4A and 4A' show details of the restrictor (constrictor).

In another implementation the flow rate regulation function can be implemented externally from the tube-shaped assembly, FIG. 1A. A preferred implementation is shown on FIG. 2C and incorporated into the blood delivering needle assembly, FIGS. 3 and 3A.

In various implementations the flow rate regulating function can be implemented at the inlet of the filter assembly or within the filter assembly or a combination of both.

Preferred implementations have one or more of the following features:

The interior of the tube assembly may be evacuated by inserting the access septum to close the upstream tube as the assembly is in a low-pressure chamber or by piercing the installed access septum with a needle connected to a vacuum pump. It is expected that vacuum can be maintained for a minimum of one year.

The device incorporates a filter or filter material assembly to which blood entering the upstream tube is exposed. In preferred embodiments the filter assembly may have 3 constituents:

- A first component that promptly disperses the blood across the entire section of the filter assembly. This is preferably a highly hydrophilic, highly porous material such as Porex filter material POR 410 or POR 4711. In another construction the upper layer of the next filter element can be conditioned to perform this function.
- A second filter element, a suitable thickness of glass fiber filter material such as Johns-Manville Micro-Strand Glass Microfibers with diameter between 1 and 4 micron and packed in density between 0.2 and 0.5 g/ml. preferably the thickness is between 10 and 20 mm.
- A third component is a micro-porous membrane able to block passage of cell debris as well as glass fiber debris and preferably permits passage of particles or molecules smaller than 0.6 micron such as plasma or serum. It also serves to prevent flow around the filter assembly and is sealed to the tube on its axial periphery via a compression ring pressing axially against a ledge internal to the tube. This third component is preferably a compliant filter material approximately ½ mm thick such as can be obtained from T.W. Tremont. Other seal methods may be used such as bonding, thermal bonding and ultrasonic welding.

The filter assembly is retained and supported axially near the middle at the tube with a perforated screen member. Suitable glass fiber density is maintained by axial compression against such screen member. The section of the tube between the input access septum and the filter assembly offers a holding chamber for the incoming blood before it travels through the filtering material.

It is thought that the low-density glass fiber filter material catches blood cells gradually by entangling at first large blood cell components and then smaller blood cell components in the space structure while permitting smaller molecules to travel through.

The invention teaches to deliver cells into and through the filter assembly with minimum and controllable force derived from a controlled pressure differential between the blood entering the filter assembly and the serum collection section of the tube. The pressure differential is controlled to induce a low velocity of the blood components beginning at the initial stage of filtering to minimize shear force on the cells, or impelling damage from collision with glass fibers of the filter assembly or with cell lodged in a tangle of glass fiber, in a manner to avoid excess hemolysis.

We know that red cells are robust when subjected to substantial pressure variations, but are very fragile in shear. This may explain why a slower flow rate reduces hemolysis. One other explanation is that red blood cells can burst on impact with the glass fibers of the filter and that the impact damage can be reduced or eliminated if the inrush speed is kept low enough. There is also possibility that cell damage is caused by a high pressure differential across the glass fiber filter, which squeezes the red cells in an extreme shear condition into the smaller filter channels causing greater shear stress that bursts the cells. In the latter instance, the longer a high pressure differential exists, the more red cell damage would occur. FIGS. 5 and 6 show that a high pressure differential persists substantially longer when the inflow rate is higher. It has been noticed during experiments that introducing a sudden high pressure differential by removing the blood inlet septum and exposing the filter inlet side to atmospheric pressure invariably resulted in an unacceptable amount of hemolysis, and so, whatever the cause or causes of red cell damage, excess pressure differential must be avoided.

This is achieved by proper dimensioning of the blood receiving volume, the flow rate controlling device (or devices) the volume and density of the glass microfibers, the total volume of the tube as well as the initial level of depressurization of the device, optimization to be found by a series of reasonable trials.

The present invention also teaches to deliver blood in a condition where early in the blood injection process a barrier is established between the parts of the tube on either side of the filter assembly. Blood entering the intake region of the filter assembly diffuses rapidly through the hydrophilic media and creates an air tight seal. Consequently the pressure condition in the tube downstream of the filter assembly is little altered by the blood injection. In contrast the pressure within the segment of the tube upstream from the filter assembly is substantially raised by the introduction of blood. This condition creates a pressure differential across the filter assembly that propels the small molecules contained in the serum to travel through the filter assembly.

The invention teaches how to regulate the pressure differential across the filter assembly. This is best achieved by control of the rate of inflow of blood as it alters the pressure in the tube upstream from the filter assembly and more specifically the region of the tube in direct contact with the filter assembly. The filter assembly is in cooperative relationship with the blood which diffuses readily through it by surface tension as well as pressure differential. Hemolysis takes place as the blood travels through the filter and is strongly affected by the pressure forces and rate of flow through the filter assembly. Little if any hemolysis takes place as blood enters the intake reservoir, it is thought, based on voluminous experience with Vacutainer™ type devices.

The pressure within the tube is altered by the introduction of the volume of blood. Considering the Ideal Gas Law:

$$PV = nRT$$

where P is the pressure of the gas, V is the volume of the gas, n is the amount of substance of gas (also known as number of moles), T is the temperature of the gas and R is the ideal, or universal, gas constant, equal to the product of Boltzmann's constant and Avogadro's constant.

In SI units, n is measured in moles, and T in Kelvin. R has the value 8.314 J·K$^{-1}$·mol$^{-1}$ or 0.08206 L·atm·mol$^{-1}$·K$^{-1}$.

Assuming constant temperature, typically human body temperature, the equation simplifies to:

$$PV = \text{Constant}$$

Initial depressurization of both ends of the tube assembly may be from 250 to 700 mmHg. Atmospheric pressure is typically 760 mmHg. Blood, upon wetting the intake side of the filter media, establishes a gas-tight surface barrier almost immediately, preventing air exchange transport between the two ends of the tube. Measurements show that about 0.5 cc are sufficient to form a seal: this occurs within 6-8 seconds when flow rate is kept low enough to prevent hemolysis, and within 1-2 seconds at higher flow rates. Thus, if the blood continues to enter at a high rate of flow the trapped air is compressed and the pressure rises accordingly. The pressure in the tube upstream from the filter assembly can rise to near atmospheric pressure while the downstream pressure remains low. This causes a high-pressure differential across the filter assembly, and red blood cells are forcefully pushed into the glass fibers, causing hemolysis. This is a condition analogous to opening the access septum to atmospheric pressure after blood injection; it is known that this results in a high level of hemolysis. This pressure condition is exemplified on FIG. 5 showing an average initial pressure differential rate of 56 mmHg/sec.

A slow rate of entry of the blood into the tube allows time for the blood to start passing through the filter media; trapped air will still be compressed by the incoming blood though much less so, resulting in a smaller pressure differential across the filter and thus minimal hemolysis. This pressure condition is exemplified on FIG. 6 showing an average initial pressure differential rate of 13.3 mmHg/sec.

Intake blood flow rates, initial pressure conditions, volumes of both segments, upstream and downstream from the filter assembly as well as the proper filter construction can be optimized to accommodate the range of plasma viscosity encountered in practice.

As the filter assembly is terminated with a submicron porosity media, the total volume of blood intake is limited to the free space upstream from the filter assembly less the volume of the filter material taking into consideration the serum filtered into the downstream tube. The serum filtration process is self-limiting and brief, 15 to 30 seconds typically.

Figure 3:
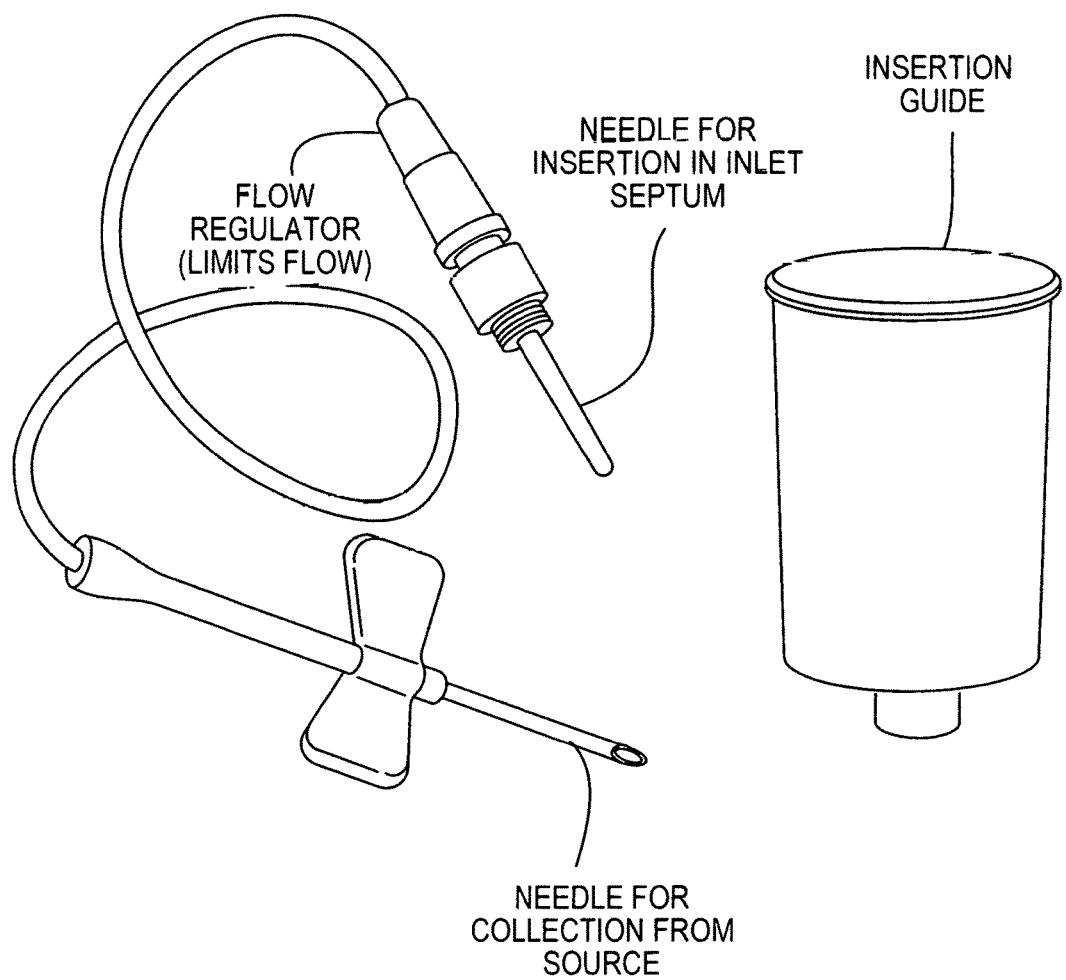
Figure 3A:
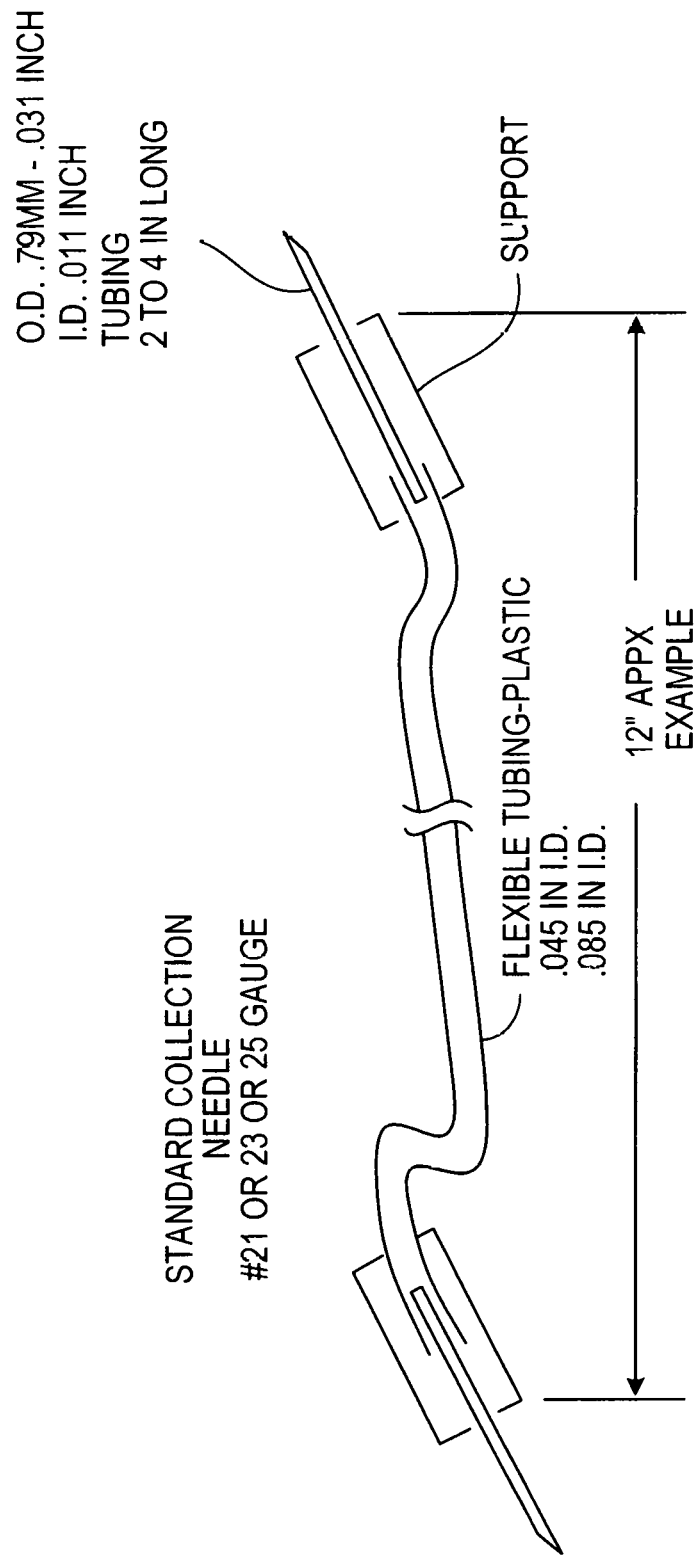
FIG. 3a illustrates the details of an example of the flexible tubing and external flow regulator to be disposed upstream of the collection/filter unit portion of the device.

Using this blood-collecting tube it is possible to carry out blood collection and separation in an efficient manner by the following procedure:

After sticking the blood-drawing needle into a blood vessel (at atmospheric pressure) or a vein (at near atmospheric pressure) the blood-collection needle punctures through the blood inlet access septum of the device. FIGS. 3 and 3a show a typical blood sampling kit: the blood drawing needle is the one with the batwing device. At this point, blood is drawn into the accumulation segment of the tube due to the negative pressure within the entire device. Blood will approximately fill that segment.

Shortly after blood enters the accumulation segment it propagates within the front part of the filter assembly creating a seal that prevents gas molecules passage through it. The entry of the blood reduces the space occupied by the molecules of air within the device.

At the start of the process, due to pre-evacuation, the entire device is at a low pressure level, possibly 100 mm Hg. The slow blood entry slowly fills the volume previously available to the air molecules and consequently the pressure within that space increases slowly according to the Ideal Gas Law.

In the preferred embodiment the device is similar to a 6 cc Vacutainer. It has uniform inside diameter of approximately 10.5 mm and wall thickness of approximately 1 mm. The blood entry chamber, flow regulator and filter assembly has a length of approximately 33 mm and the overall tube approximately 80 mm.

The filter assembly is formed with approximately 0.35 gram of 108 A or 108 B Micro-Strand Glass Microfibers from Johns Manville or equivalent with nominal diameter 1.8 micron having a net density 0.15 and 0.5 and preferably approximately 0.027 gram per cubic centimeter. (In other embodiments 0.5 grams of the microfibers can be used, or within the 0.35 gram to 0.5 gram range, 0.415 grams bay be used.)

The glass fiber segment may be covered at its entry with a highly hydrophilic filter layer such as Porex™ filter material POR 41210 or POR 4711 and at its exit with a 0.6 micron porosity filter. (In another embodiment filter material of 1.0 micron porosity may be used to take advantage of better tear properties that it may have.)

A flow control regulator is located between the blood entry access septum and the filter assembly segment. It can be a cup shaped thin cylindrical element holding in its center a capillary flexible tubing with 0.25 mm inside diameter and a length of 40 or 50 mm as shown on FIG. 3A.

The rate of blood flow entering the device through the access septum is quite low, approximately 0.05 cc/sec. to 0.1 cc/sec and when the blood has approximately filled the accumulation segment the blood-collecting needle can be disconnected from the access septum in a manner that does not permit air or a gas to penetrate the device. This process takes form 15 to 30 seconds.

The pressure differential acting on the blood against the filter assembly rises slowly in a passive manner to approximately 330 mm Hg and settles to approximately 150 mmHg within 1 to 3 minutes when the serum separation can be finalized by permitting air at atmospheric pressure to enter the serum end of the tube.

Due to this pressure difference, the blood gains a tendency to flow through the flow rate regulation segment and into the filter assembly and toward the downstream end of the tube. The flow rate regulator prevents rapid inrush of blood cells and serum molecules. However, because the filter assembly captures cells and only permits through passage to molecules or particles smaller than 0.6 micron only serum or plasma or hemoglobin are allowed to pass through and accumulate into the downstream end of the tube. Thus, separation of the blood is performed shortly after it has been collected.

Upon completion of serum collection, the serum access septum can be pierced or separated for plasma collecting and further processing.

The flow regulator device is preferably in the form equivalent to a length of channel of small cross section (though many times the width of blood cells). The blood flow rate needs to be such that blood entering the glass fiber filter section do not cause damage to the red cells previously located in the maze of glass fibers forming the main part of the filter. The flow control device permits a steady flow rate and prevents a burst flow from taking place. The process can accommodate the expected range of blood viscosities.

In another preferred embodiment the flow rate controller is incorporated in the blood-collection needle assembly and consists of a capillary restricted channel approximately 25 to 50 mm long a with diameter between 0.25 mm and 0.30 mm.

In another preferred embodiment the blood flow rate controller is in the form of a circular channel created when a screw is inserted in a smooth cylinder of mated diameter. The section of the channel thus created and its length—the number of turns times the diameter-limits the rate of flow possible for a fluid of defined viscosity and a defined pressure differential acting on the fluid. Such a screw constrictor is shown on FIG. 2D and FIG. 4A. The channel in the preferred embodiment has a section equivalent to that of a tube of diameter 0.25 mm and 0.30 mm and a length 25 and 50 mm.

Flow Rate and Flow Geometry

The preferred flow rate is from approximately 2 to 10 cc per minute and preferably 3 to 6 cc per minute to a volume of 1 to 2 cc preferably 1.5 cc.

The capillary restriction flow rate for blood can be derived from the Hagen-Poiseuille law:

$Q = K \cdot \Delta P \cdot \pi R^4 / 8L\mu$

Where:
K: is a constant
Q: flow rate
R: capillary radius
L: capillary length
ΔP: pressure drop
μ: blood viscosity Considering that it is desirable to limit the pressure differential and maintain a practical flow rate it is possible to select alternate tube diameters and corresponding tube length for either internal or external flow rate control device or baffle disc, located on the inlet side of the filter assembly, fitted with one or numerous pinholes.

If one chooses an equivalent baffle with a single pin hole the Hagen-Poiseuille law suggests a 1 mm thick baffle with 0.1 mm diameter hole or a 1/16 inch thick baffle with a 0.005 inch diameter hole as shown on FIG. 2E.

If one might seek to preserve the 12-inch flexible tube length of commercial blood drawing assemblies, and accomplish the flow rate control in a blood-drawing implementation, just by special construction of the tubing, effectively making the tubing itself the limiting control element, the Hagen-Poiseuille law instructs that the tubing should have an inner diameter of approximately 0.015 inches, considerably smaller than that of commercial blood drawing devices. An alternate design is the introduction of a section of tubing less than the full length of the blood drawing tube that has reduced diameter. According to a preferred implementation, a 2 to 4 inch section of 0.012 inch diameter tubing is employed within the 12 inches length from needle to needle, as herein presented.

The Hagen-Poiseuille law is applicable to Newtonian fluids. Blood is a non-Newtonian fluid and this is specially expressed when capillaries or rigid flow channels are either too narrow or too long. It has been verified experimentally that the Hagen-Poiseuille law is useful for the present purposes, and is especially applicable to the preferred flow constrictor, of the order of 0.011 inch internal diameter and 2 inches length.

It has been verified experimentally that the law does not apply to capillaries 0.004 or 0.005 inch (100 and 125 micron) in inside diameter.

It has also been verified that extending the length of a rigid tubing to 24 inches damages red cell and causes hemolysis.

Preferred dimensions for a tubular limiting control element are between about ½ inch and 4 inches in length and ID between about 0.008 and 0.013 inch.

In another way the rate of increase of the pressure differential between the blood entry segment of the device and the serum collection segment can be regulated with the insertion of a compressible element working as an intake pressure buffer in the blood entry segment of the device.

In another way the rate of increase of the pressure differential between the blood entry segment of the device and the serum collection segment can be facilitated with appropriate volume relationships defined by the axial location of the filter assembly.

Pressurized Operation

In other uses of control of pressure or flow rate upstream of a blood filter using a simple flow rate or pressure control element or section as herein described, the pressure differential across the filter assembly is obtainable by pressurizing the blood upstream of the control element or section to above atmospheric pressure and venting the downstream side of the filter assembly to atmosphere.

Highly useful blood separators that implement this approach can make use of a blood container, e.g., a conventional evacuated blood collection tube, as a novel one-stroke piston to produce the pressure upstream of the blood. The blood separator device may take the form of an open ended tube that precedes a filter assembly, into which the blood container slides. It makes sealed engagement with the tube wall to produce pumping action. During this action, the filter assembly and following filtrate collector are closed to the atmosphere. The motion of the container is employed to increase air pressure throughout the closed volume. Later, upon venting the filtrate collector, the air pressure above the blood in the container is employed to drive the blood through the control element or section and filter assembly into the then-vented collector.

Figure 7A:
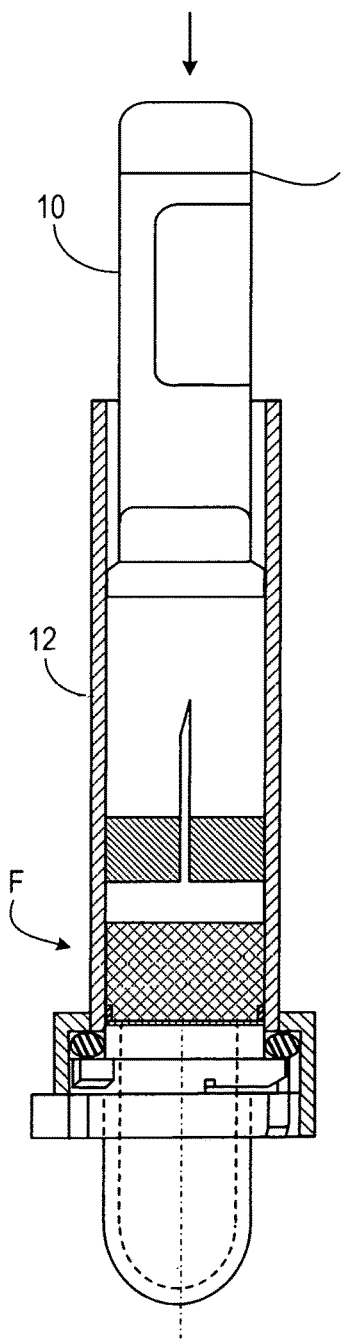
FIG. 7A shows a collection tube in process of being inserted into the filter device.
Figure 8:
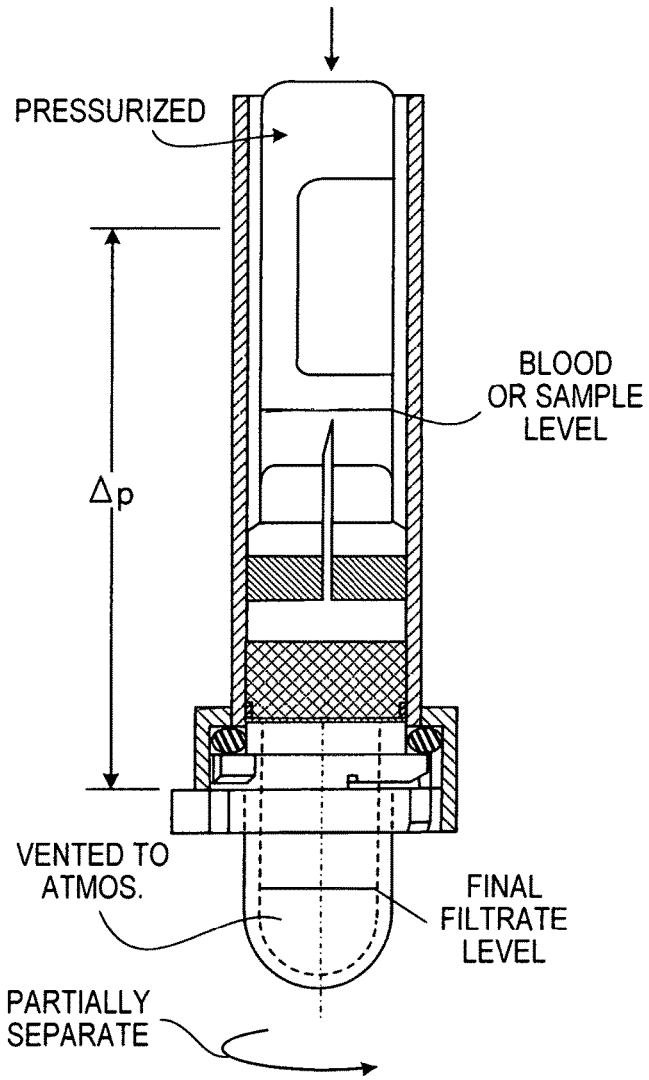
FIG. 8 is a longitudinal cross-section of a filter device assembly and a collection tube holding blood fully inserted into the filter device and following opening the "Serum Holding Chamber" to atmospheric pressure.
Figures 9A, 9B, 9C:
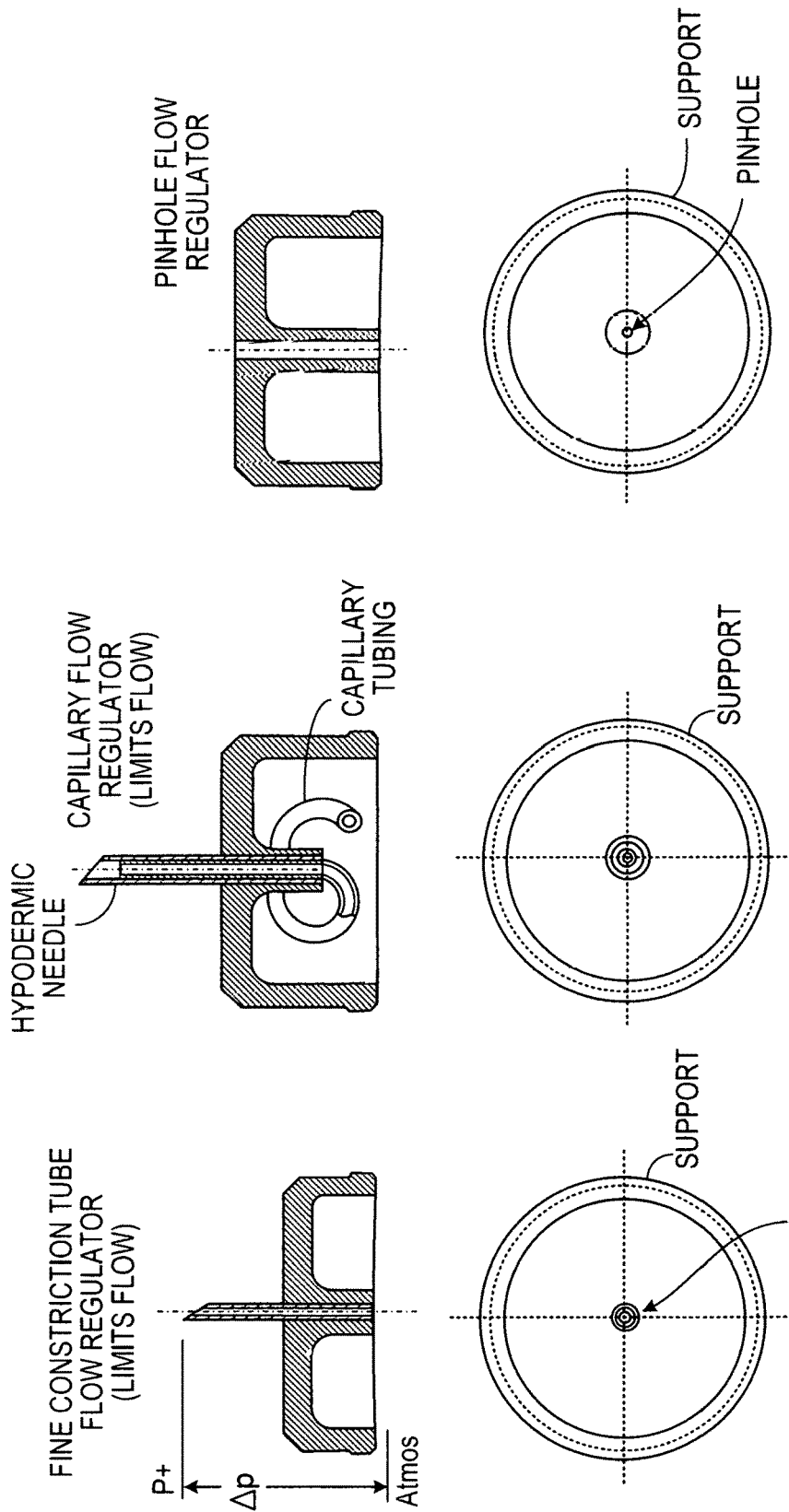
FIGS. 9A, 9B and 9C show blood-transfer-flow regulator devices located above the glass fiber filter.

Referring to FIGS. 7-9, an implementation is shown in which blood separating device 8 is used with a conventional evacuated collection tube 10 such as available from Becton Dickinson and Company under the trademark Vacutainer™). When tube 10 is inverted with its rubber access seal 10a down, previously collected blood may reach level L, occupying 70% of the collection space within the tube.

At this stage the filtrate collector 14 is sealed to the body of the blood separator device 8. Holding the device 8 vertically, open end up, a user introduces the inverted collection tube 10 and presses it gently down into the larger tubular body 12 of the separator device 8 to pierce the septum 10a of the collection tube 10 with an opposed hypodermic needle 20 that forms a capillary flow regulator or control element. The downward stroke of the collection tube 10 at first causes air only in the closed volume below to be compressed. As shown on FIG. 8 the collection tube 10 may travel to be fully inserted in the separating device 8. But when the septum 10a of the collection tube 10 reaches the protruding hypodermic needle 20 and is pierced by it, pressure within the device 8 and the collection tube 10 is equilibrated.

For initiating filtering action, the Serum Collection Chamber (filtrate collector) 14 is partially then opened, permitting air to escape from the collector and bringing the region downstream from the filter assembly F to atmospheric pressure, thus creating a pressure difference across filter assembly F.

With this occurrence, air pressure above the blood within the collection tube 10 becomes relatively higher than that below the Filter assembly F. This sets up a second automatic equilibrating action, in which the higher air pressure in the collection tube 10 forces flow of blood out of the collection tube, downwardly through the hypodermic needle 20, into the space above the filter assembly F. In this implementation the pressure differential above atmospheric pressure thus drives blood through the flow control and the filter media.

Preferably the compressed volume is small compared with the total original volume of the device. When the collection tube is pushed to its stopped position, the "free" remaining volume of the device may be quite small.

The "free remaining volume" consists of the Serum Collection Chamber 14 and the filter assembly F as well as the flow regulation assembly 20.

The established pressure differential is controlled by the Ideal Gas Law:

$$PV = \text{Constant.}$$

The initial conditions when the collection tube is about to be introduced into the device P is atmospheric pressure.

Assuming that the inside diameter of the internal diameter of the main body is 11.0 mm at its open end is about equal to the diameter of the deformable septum of the evacuated collection tube (Vacutainer™) such that the collection tube can be inserted without difficulty with alignment to its full length of 50.5 mm. The inner diameter of the main body 12 is slightly tapered such that it can easily be manufactured by injection molding or otherwise. If the inside diameter of the main body, 50 mm downward from the entry level is 10.5 mm, the volume of air displaced by the insertion of the collection tube is 4.58 cc.

The serum collection chamber is approximately 0.5 cc and the void volume of the filter assembly approximately 1.0 cc with the pressure control and coupling region adding up to 0.75 cc, the total volume remaining adds to 2.25 cc.

The original air volume was 6.83 cc.

The "1.8 cc Vacutainer" has inner volume equal to 2.25 cc. and when filled with 1.8 cc of blood yields a void volume 0.45 cc.

The final volume of air is therefore 2.25+0.45=2.7 cc.

The Ideal Gas Law indicates that the pressure in the compressed device shall be:

$$1 \times 6.83/2.7 = 2.5 \text{ atmosphere}$$

This is the pressure of the air inside the blood collection tube.

When the "serum collection chamber" is opened to atmospheric pressure the pressure differential propels blood out of the blood collection tube.

Inside the Vacutainer the Ideal Gas Law applies. Prior to opening the serum collection chamber to atmospheric pressure, the conditions were:

$$P = 2.5 \text{ atmosphere}$$

$$V = 0.45 \text{ cc}$$

Opening the "serum collection chamber" to atmospheric pressure will bring that pressure to the inside of the Vacutainer and the air volume will become:

$$V = 1.125 \text{ cc}$$

And approximately 0.675 cc of blood is forced out through the flow control section, the filter and finally pushing the serum or plasma into the serum collection chamber.

Approximately 0.25 cc of plasma is collected into the "serum collection chamber".

In respect of flow rate and flow geometry, the considerations and findings described under the heading FLOW RATE AND FLOW GEOMETRY apply.

A number of embodiments of the invention have been described. Nevertheless, it will be understood that various modifications may be made without departing from the spirit and scope of the invention. For example, the flow rate or pressure differential limiting control element or device may take the form of a compliant tube wall section that tends to expand outward to increase volume in response to pressure. Accordingly, other embodiments are within the scope of the following claims.

What is claimed is:

1. A filtering device for filtering blood to obtain serum or plasma in a container, the container having access at both ends, a filter located within the container, and a flow rate or pressure differential limiting control element or device, the limiting element or device being located upstream of the filter and including a flexible tubing length located outside of the container, the control element or device being constructed to limit increase in the pressure differential rate of change across the filter to about 10 mmHg thus substantially eliminating hemolysis associated with the filter.

2. The filtering device of claim 1 in which the container is partially evacuated.

3. The filtering device of claim 2 wherein the limiting control element or device is located outside the container.

4. The filtering device of claim 3 wherein the limiting control element or device is integral with a blood drawing needle assembly.

5. The filtering device of claim 1 wherein the container during operation is partially pressurized.

6. The filtering device of claim 1 wherein the limiting control element or device is located inside the container.

7. A filtering device for filtering blood to obtain serum or plasma, comprising a pre-evacuated container, a filter located within the container, and a flow rate or pressure differential limiting control element or device comprises a selected length of capillary tubing.

8. The filtering device of claim 7 wherein the flow rate or pressure differential limiting control element or device is in the form of a pin hole or pin holes in a flow-blocking disk.

9. The filtering device of claim 7 wherein the control element or device comprises a fine mesh or porous foam.

10. The filtering device of claim 7 wherein the control element or device comprises a passage defined by a screw like segment.

11. A filtering device for filtering blood to obtain serum or plasma, comprising a pre-evacuated container, a filter located within the container, and a flow rate or pressure differential limiting control element or device constructed to limit differential pressure across the filter by restricting flow toward the filter, wherein the limiting element or device is constructed to passively limit increase in the pressure differential rate of change across the filter to about 10 mmHg and thereby substantially reduce hemolysis associated with the filter.

12. The filtering device of claim 11 wherein the limiting control element or device is preceding the filter and limits entering flow-rate of whole blood drawn from a living being.

13. The filtering device of claims 11 wherein it has a limiting control element or device preceding the filter that defines entering pressure increase rate in whole blood drawn from a living being.

14. The filtering device of claims 11 wherein it is portable or hand held, and includes a volume sized for blood drawn from a living being.

15. The filtering device of claims 11 wherein the material of the filter comprises glass microfibers and micro-porous membrane on a locating support.

16. The filtering device of claims 11 in which the container includes a tube.

17. The filtering device of claims 11 having an access septum at the inlet end of the container.

18. The filtering device of claim 17 having an access septum at the outlet end of the container.

19. The filtering device of claim 11 wherein the flow rate limiting control element is integral with a blood drawing needle assembly.

20. A method of obtaining blood serum or plasma using the filtering device of claim 11.

21. A device comprising a pre-evacuated container, and a flow rate limiting control element limiting pressure and including capillary restriction for blood flow into the container and being constructed to provide said capillary restriction according to the Hagen-Poiseuille law for a designed capillary radius, capillary length and pressure drop.

22. The device of claim 21, wherein the pre-evacuated container includes a tube.

23. The device of claim 22, wherein the tube includes inlet and outlet ends with access at both ends.

24. The device of claim 21 including a blood drawing needle assembly.

25. The device of claim 21, wherein the blood drawing needle assembly includes said capillary restriction.

26. A method of obtaining blood serum or plasma by filtering blood using the device of claim 21.

* * * * *